US010844382B2

(12) United States Patent
MacKenzie-Lamb et al.

(10) Patent No.: US 10,844,382 B2
(45) Date of Patent: Nov. 24, 2020

(54) DNA CONSTRUCTS FOR MANUFACTURING BIO-THERAPUETIC POLYPEPTIDES FOR USE IN ANIMAL VACCINES AND THERAPEUTICS

(71) Applicant: MicroSynbiotiX, Ltd., Cork City, Cork (IE)

(72) Inventors: Viktor Antonio MacKenzie-Lamb, Basel (CH); Simon Porphy Jegathese, Cork (IE); Kwang-Chul Kwon, La Jolla, CA (US)

(73) Assignee: MicroSynbiotiX, Ltd., Cork (IE)

( * ) Notice: Subject to any disclaimer, the term of this patent is extended or adjusted under 35 U.S.C. 154(b) by 0 days.

(21) Appl. No.: 16/092,279

(22) PCT Filed: Apr. 11, 2017

(86) PCT No.: PCT/US2017/026995
§ 371 (c)(1),
(2) Date: Oct. 9, 2018

(87) PCT Pub. No.: WO2017/180616
PCT Pub. Date: Oct. 19, 2017

(65) Prior Publication Data

US 2019/0142924 A1 May 16, 2019

Related U.S. Application Data

(60) Provisional application No. 62/320,878, filed on Apr. 11, 2016, provisional application No. 62/378,534, filed on Aug. 23, 2016.

(51) Int. Cl.

| | |
|---|---|
| ***C12N 15/63*** | (2006.01) |
| ***C12N 15/79*** | (2006.01) |
| ***C12N 15/90*** | (2006.01) |
| ***C12N 15/113*** | (2010.01) |
| *A61K 39/00* | (2006.01) |

(52) U.S. Cl.
CPC .......... *C12N 15/1131* (2013.01); *C12N 15/63* (2013.01); *C12N 15/79* (2013.01); *C12N 15/902* (2013.01); *A61K 2039/552* (2013.01); *A61K 2039/6075* (2013.01); *C12N 2310/531* (2013.01)

(58) Field of Classification Search
None
See application file for complete search history.

(56) References Cited

U.S. PATENT DOCUMENTS 7,186,560 B2 * 3/2007 Maliga .................... C12N 9/22 435/320.1
7,678,561 B2 * 3/2010 Mayfield ................ C12N 15/79 435/257.2
2005/0080032 A1 4/2005 Gross et al.
2013/0164850 A1 6/2013 Sourdive
2014/0335562 A1 * 11/2014 Fang .................. C12N 9/0004 435/69.1

FOREIGN PATENT DOCUMENTS

| | | | |
|---|---|---|---|
| KR | 101273264 | B1 | 6/2013 |
| WO | 2008/021223 | A2 | 2/2008 |
| WO | 2010/078156 | A1 | 7/2010 |

OTHER PUBLICATIONS

PCT/US2017/026995 International Search Report dated Jul. 17, 2017.
Kuzyk, et al. "An efficacious recombinant subunit vaccine against the salmonid rickettsial pathogen Piscinckettsia salmonis," Vaccine, Mar. 21, 2001, vol. 19, pp. 2337-2344.
Negrell et al. "Notes on Ichthyophthirius multifiliis, a ciliate parasitic on freshwater fishes, with some remarks on possible physiological races and species." Transactions of the American Microscopical Society, Oct. 1976, 95 (4):607-613.
EP17782972.8 Extended European Search Report dated Nov. 7, 2019.
Rasala et al. "Improved heterologous protein expression in the chloroplast of Chlamydomonas reinhardtii through promoter and 5' untranslated region optimization," Plant Biotechnology Journal, 2011, 9:674-683.
Bertalan et al. "A rapid, modular and marker-free chloroplast expression system for the green alga Chlamydomonas reinhardtii," Journal of Biotechnology, Feb. 2015, 195:60-66.
Mayfield et al. "Expression and assembly of a fully active antibody in algae," PNAS, Jan. 21, 2003, 100 (2):438-442.
Nigrelli et al. "Notes on Ichthyophthirius multifiliis, a ciliate parasitic on fresh-water fishes, with some remarks on possible physiological races and species," Transactions of the American Microscopical Society, Oct. 1976, 95 (4):607-613.

* cited by examiner

*Primary Examiner* — Jason Deveau Rosen
(74) *Attorney, Agent, or Firm* — Wagenknecht IP Law Group, PC

(57) ABSTRACT

A nucleic acid constructs including a heterologous nucleotide sequence operably linked to a constitutively active promoter; a 5' recombination sequence at a 5' end of the construct and a 3' recombination sequence at a 3' end of the construct, wherein the recombination sequences are configured for homologous recombination into a genome of a microalgal host cell; and optionally a bacterial 5' untranslated region (5'UTR) between the 5' recombination sequence and the promoter, and a bacterial 3' untranslated region (3'UTR) between the 3' recombination sequence and the heterologous nucleotide sequence.

10 Claims, 16 Drawing Sheets

Specification includes a Sequence Listing.

SEQ ID NO: 1: Synthetic construct providing VP28 Sense joined to VP29 antisense via a linker configured to form a loop tctagaATGGATCTTTCTTTCACTCTTTCGGTCGTGTCGGCCATCCTCGCCATCACTGCTGTGATTGCTGTATTT
ATTGTGATTTTTAGGTATCACAACACTGTGACCAAGACCATCGAAACCCACACAGACAATATCGAGACAAA
CATGGATGAAAACCTCCGCATTCCTGTGACTGCTGAGGTTGGATCAGGCTACTTCAAGATGACTGATGTGT
CCTTTGACAGCGACACCTTGGGCAAAATCAAGATCCGCAATGGAAAGTCTGATGCACAGATGAAGGAAG
AAGATGCGGATCTTGTCATCACTCCCGTGGAGGGCCGAGCACTCGAAGTGACTGTGGGGCAGAATCTCAC
CTTTGAGGGAACATTCAAGGTGTGGAACAACACATCAAGAAAGATCAACATCACTGGTATGCAGATGGTG
CCAAAGATTAACCCATCAAAGGCCTTTGTCGGTAGCTCCAACACCTCCTCCTTCACCCCCGTCTCTATTGAT
GAGGATGAAGTTGGCACCTTTGTGTGTGGTACCACCTTTGGCGCACCAATTGCAGCTACCGCCGGTGGA
AATCTTTTCGACATGTACGTGCACGTCACCTACTCTGGCACTGAGACCGAGTAAaagggcgaattcgcccttAC
ACAAAGGTGCCAACTTCATCCTCATCAATAGAGACGGGGGTGAAGGAGGAGGTGTTGGAGCTACCGACA
AAGGCCTTTGATGGGTTAATCTTTGGCACCATCTGCATACCAGTGATGTTGATCTTTCTTGATGTGTTGTTCC
ACACCTTGAATGTTCCCTCAAAGGTGAGATTCTGCCCCACAGTCACTTCGAGTGCTCGGCCCTCCACGGGA
GTGATGACAAGATCCGCATCTTCTTCCTTCATCTGTGCATCAGACTTTCCATTGCGGATCTTGATTTTGCCCA
AGGTGTCGCTGTCAAAGGACACATCAGTCATCTTGAAGTAGCCTGATCCAACCTCAGCAGTCACAGGAAT
GCGGAGGTTTTCATCCATGTTTGTCTCGATATTGTCTGTGTGGGTTTCGATGGTCTTGGTCACAGTGTTGTG
ATACCTAAAAATCACAATAAATACAGCAATCACAGCAGTGATGGCGAGGATGGCCGACACGACCGAAAGA
GTGAAAGAAAGATCCATgctgagc

FIG. 3

| WSSV (AF440570) ORF No. | Protein name | Localization on virion | WSSV (AF440570) ORF No. | Protein name | Localization on virion |
|---|---|---|---|---|---|
| WSSV019 | VP35 | NC | WSSV324 | VP53C | NC |
| WSSV027 | VP362 | nd | WSSV326 | VP136A | NC |
| WSSV051 | VP448 | nd | WSSV339 | VP13A | nd |
| WSSV052 | VP180 | Env | WSSV349 | VP14 | nd |
| WSSV059 | VP24 | nd | WSSV359 | VP22 | nd |
| WSSV065 | VP12 | Teg | WSSV362 | VP39A | Teg |
| WSSV067 | VP53A, | Env | WSSV364 | VP51, VP51C | NC |
| WSSV092 | VP110 | Env | WSSV367 | VP26 | Teg |
| WSSV094 | VP160B | nd | WSSV377 | VP16, VP13B | Env |
| WSSV134 | VP36A | Teg | WSSV381 | VP56, VP60A | Env |
| WSSV171 | VP538 | nd | WSSV383 | VP90 | Env |
| WSSV192 | VP337 | nd | WSSV388 | VP75 | NC |
| WSSV253 | VP32 | Env | WSSV394 | VP11 | Env |
| WSSV254 | VP320 | nd | WSSV395 | VP39, VP39B | Env |
| WSSV264 | VP187 | Env | WSSV396 | VP31 | Env |
| WSSV269 | VP15 | NC | WSSV419 | VP664 | NC |
| WSSV271 | VP124 | Env | WSSV445 | VP128 | Env |
| WSSV275 | VP73, VP76 | NC | WSSV449 | VP368 | Env |
| WSSV293 | VP41A | Env | WSSV473 | VP19 | Env |
| WSSV294 | VP51A | Env | WSSV474 | VP60B | NC |
| WSSV298 | VP41B | Env | WSSV480 | VP28 | Env |
| WSSV304 | VP216 | nd | WSSV502 | VP95 | Teg |
| WSSV309 | VP36B, VP37 | NC | WSSV524 | VP136B | nd |
| WSSV311 | VP51B, VP52B | Env | | WSV010* | nd |
| WSSV314 | VP38, VP38A | Env | | | |

*This ORF was reported in the WSSV China isolate (GenBank accession number AF332093), but it was not predicted to be an ORF in the WSSV TW genome (GenBank accession number AF440570).

NC: nucleocapsid, Env: envelope, Teg: tegument; nd: not yet determined or the protein's status is still controversial.

**Three P. monodon cellular protein genes not listed in the above Table include the pmCBP (chitin-binding protein [54]), pmRACK1 (receptor for activated C kinase-1, GenBank accession number EF569136), and pmRab7 (GenBank accession number DQ231062) which had been reported related to WSSV infection are also included in the yeast two-hybrid prey library and were assayed in the present study.

doi:10.1371/journal.pone.0085779.t003

FIG. 4

| PULSE DURATION | | GENE | RELATIVE TRANSCRIPTION RATE |
|---|---|---|---|
| 10' | 20' | | |
| | | — rrn | 1.000 |
| | | — psbA | 0.132 |
| | | — rbcL | 0.312 |
| | | — psaB | 0.013 |
| | | — atpA | 0.018 |
| | | — atpB | 0.043 |
| | | — tufA | 0.030 |
| | | — rpl16 | 0.049 |
| | | — pUC | — |

SEQ ID NO: 2 - Synthetic construct formed by fusing the 463bp Chlorella 16S rrn promoter to the T7g10 5'UTR AAAAGAAAAAAATAAAGAAAGATTTTAAAGCAGTTTTTGATTCTAGAT
CTAGAAAAAACAATATTTTCTTTTAGAACATAAACGGTCTAAAATTTAGT
TTAAACTGTAGGCATCCTATTTACAAATTACATAGTTTTTTTAGTAAAAA
AAATGTATTTTTTCCAAAAGTTAAAAGTTTGAAAAAATAAATTTAAACA
CAAAGACCAGAACAAAAAAAAACTTTTCTCAACAAAAAATAGAATTAA
AATCAAAGTTAAATTCGTAAATTTTAACTTTGATTCTTCTGGAAGTGCAA
CTACTTTCCGTTTAGCTGGTTGAAATCTTTAGTATAAATTTTTTTTAAGC
AAAAAATTTAATTTAACTATGATAAATTTAAAAATTAAAGCAAGGAAAA
AAAGAAGAGAGAGGAAGACTGGTTTGACTTTTTTTTATTAAAGATAC
ATTACTAAGTGTGAAAACAAAAAATTTTCATGGAGAGTTTGATCCTGGCT
CAGGATGAA

FIG. 7

SEQ ID NO: 27 - 3' UTR of Chlorella vulgaris

CCTTTTAAAGGATAAAAAAACCTTAAGAAAAAAACAAAGTTTTTCTTAAGTACTCCA
ATCCTTCTTTCTTTTTTTATTCCCATTAAATTGAATAAAAATTAAACGTTTTCTTACT
TTAATGAGAATATAAATTAAGATGATTTCCGTTTTTTGAAATCCAGTTTTTGGTTTTT
TTTTTTCCTTCTTTTTTTTTTTATAAAAAAAAAAGATCAAAATGAATCAAAAACTAATA
GAAAAAAAACGGAATTTGAAGAATTGATTCATTTTTTACATGTGCATGAGTCACTA
GCTTGCTTTTTTAGTGCACTAACCTCTTCTCCAAAAATTTTTCAAACCAAAATTTA
TGGGAAGAAGAGAGTGGGAAAAAACAAC

FIG. 8

TABLE 2: Chloroplast promoter sequences having homology to prokaryotic bacterial promoter elements

| Seq ID | Organisms and Genes | | minus 35 region | minus 10 region |
|---|---|---|---|---|
| | Structurally and Functionally Defined: | | | |
| | **E. coli Consensus Sequence** | | **TTGACA** | **TATAAT** |
| 3 | N. tabacum rbcL | AAGTAAAAAAGAAAAATTGGG | **TTGCCTA**TATATATGAAGAGTA | **TACAAT**AATGATGTATTTGGCAAATC |
| 4 | N. otophora rbcL | AAGTAAAAAAGAAAAATTGGG | **TTGCGCT**ATATATATGAAAGAGTA | **TACAAT**AATGATCTATTTGGCAAATC |
| 5 | N. tabacum atpB | TCAGGTTCGAATTCCATAGAA | **TAGATAA**TATGGATGGGATTGTC | **TATAATG**ATAGACAAATGAAAGACTT |
| 6 | N. otophora atpB | TCAGGTTCGAATTCCATAGAA | **TAGATAA**TATGGATGGGATTGTC | **TATAAT**GATAGACAAATGAAAGACTT |
| 7 | N. tabacum 5S rRNA | GGTGTCCCCTCCAGTCAAGAA | **TTGGGG**CCTCACAATCACTAGCCAA | **TATGCT**TTTCTCTCATGCCTTTCTTC |
| 8 | N. tabacum 16S rRNA | AGTTGTTCAAGAATAGTOQCG | **TTGAGT**TTCTCGACCCTTTGACT | **TAGGAT**TAGTCAGTTCTATTTCTCGA |
| 9 | tRNA (glY) | TGATTACCACAATTCCCCTGT | **TCGACA**AAAGTTGCATTTGTA | **TACAAT**AATCGGATTGTA |
| 10 | Maize rbcL | AATAAAGATTAGGGTTTGGG | **TTGCGC**TATATCTATCAAGAGTA | **TACAAT**AATGATGGATTTGGTGAATC |
| 11 | Maize atpB | AATACTAAGAAAATTCTCTG | **TTGACA**GCAATCTATOCTTCACAG | **TAGTAT**ATATTTTGTATATCGGGTC |
| 12 | Maize 16s rRNA | ATGGATAGGAGGCTTGTGGGA | **TTGACG**TGATAGGGTAGGGTTGOC | **TATACT**GCTGGTGGCGAACTCCAGGC |
| 13 | tRNAVal(l) | TCCTATTTTCCATAGGACCGG | **TTGACA**ATTGAATOCAATTTTTCCCAT | **TATTTG**ACTGTCCATAATAGTGOCGA |
| 14 | tRNAVal(2) | AAGCCCGAAAGAGTGGCC | **TTGCGT**TTCTCGCCCCTTTGCCT | **TAGGAT**TCGTTAATTCTCTTTCTCGA |
| 15 | tRNA (His) | TCAGAATAAATAGAATAATAA | **TGAATG**AAAAAGAGAAAATOCT | **TGAATG**AAAAAGAGAAAATOCT |
| 16 | Spinach rbcL | AAACCAACGGTTACGGTTGGG | **TTGCGC**CATATATATGAAAGAGTA | **TACAAT**AATGATGTATTTGCCGAATC |
| 17 | Spinach atpB | AATACTAATAAATTCTTTG | **TTGACA**GTGGTATATGTTGTATATG | **TATATC**CTAGATGTGAAAATATGC |
| 18 | **C. reihnhardtii atpA (algae)** | AAGTAATGGTTCACCC | TTGTCATATTTAAATAC | **TAAAAT**TCATTTGCC |

FIG. 9

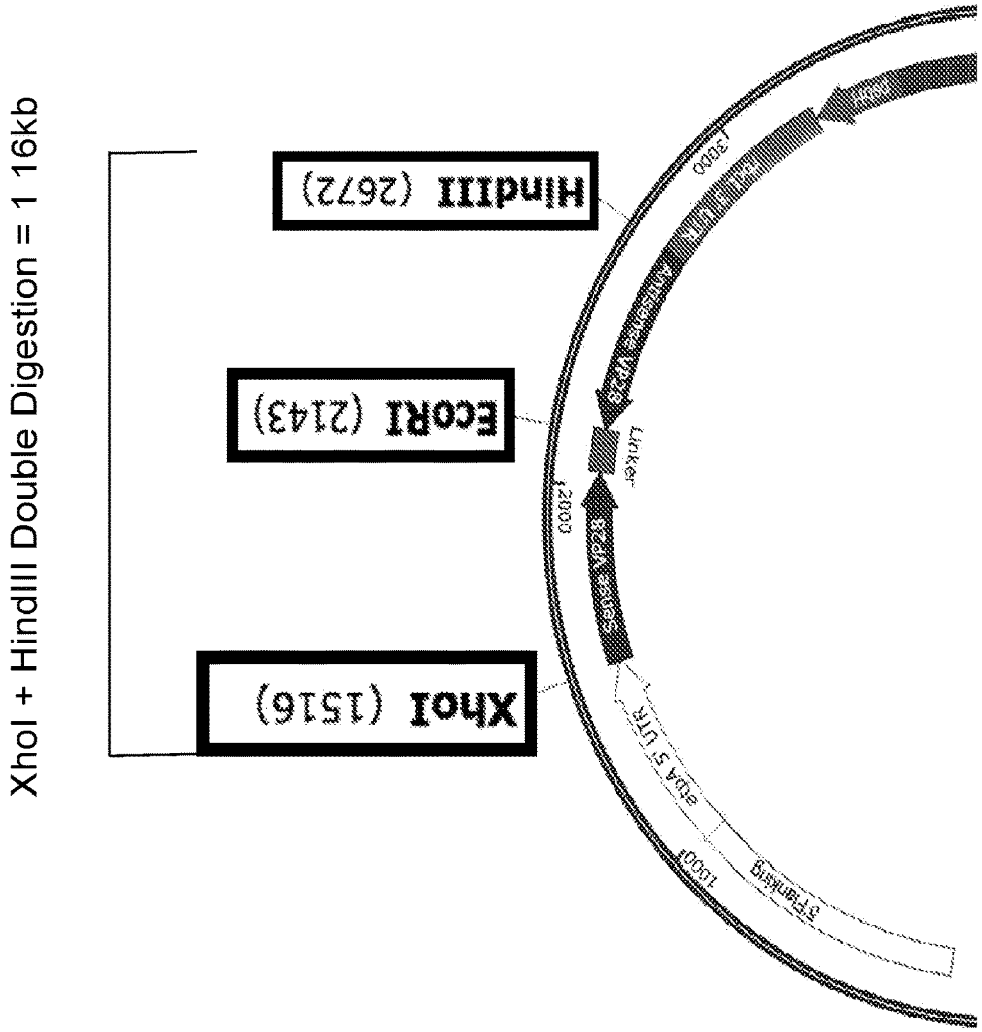
FIG. 12
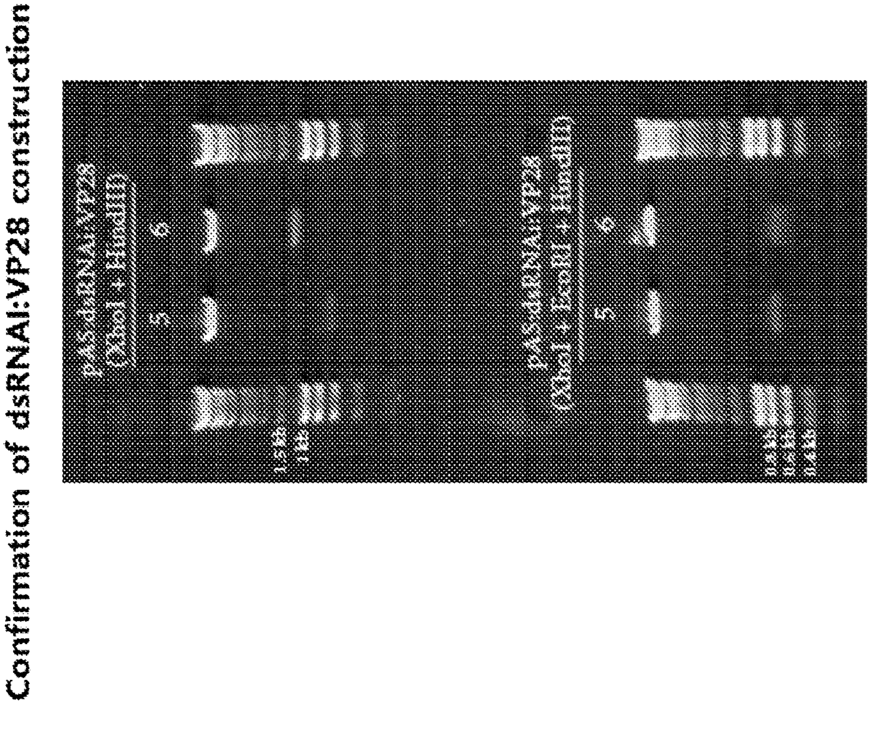

DNA CONSTRUCTS FOR MANUFACTURING BIO-THERAPUETIC POLYPEPTIDES FOR USE IN ANIMAL VACCINES AND THERAPEUTICS

CROSS REFERENCE TO RELATED APPLICATIONS

This application is a US national phase application under 35 USC § 371 of International Patent Application No. PCT/US2017/026995, filed Apr. 11, 2017, which itself claims benefit of priority to US provisional patent application no. 62/320,878, filed Apr. 11, 2016, and US provisional patent application no. 62/378,534, filed Aug. 23, 2016, the entire content of each is herein incorporated by reference in its entirety.

REFERENCE TO SEQUENCE LISTING SUBMITTED ELECTRONICALLY

The official copy of the sequence listing is submitted electronically via EFS-Web as an ASCII formatted sequence listing with file "PCTUS2017026995_SEQ_UD" created on 11 Apr. 2017, filed on 9 Oct. 2018 and having a size of 19 Kilobytes. The sequence listing contained in this ASCII formatted document forms part of the specification and is herein incorporated by reference in its entirety.

TECHNICAL FIELD

The invention relates to nucleic acid constructs for producing heterologous agents in host cells and more specifically to nucleic acid constructs having a heterologous nucleotide sequence operably linked to a constitutively active promoter; and a set of flanking recombination sequences at opposing ends of the construct for homologous recombination into a genome of a microalgal host cell.

BACKGROUND OF THE INVENTION

One of the greatest challenges for the growing aquaculture industry is managing disease. Some viral and bacterial infections have the potential to wipe out entire farms and result in millions of dollars of losses. The use of vaccinations, antibiotics, and antimicrobial agents are the most common methods of managing disease in aquaculture, and have a global annual cost to the industry of greater than 1 billion USD, with vaccines alone accounting for 450 million USD. Currently, the most commonly used method of vaccination is hand-held injection. The approach is labor intensive and expensive. It requires the fish to be of a certain size and maturity. Even though the process can be automated and anesthesia is often administered beforehand, there is still high mortality in this stressful procedure. For many species (in particular, crustaceans) the use of injectable vaccination is completely impractical, leaving few alternative strategies available for disease management in these species.

The most ideal method of vaccinating fish/shrimps is by oral vaccination. Oral administration is a very simple and elegant way to deliver vaccines, as it mimics the natural feeding of the fish/shrimps and allows the vaccine/recombinant therapeutic protein to be delivered directly to the digestive tract. However, several problems persist with current oral vaccination approaches, including provision of suitable antigen concentration in the oral vaccine to elicit an immune response. Also, current oral vaccines are packed with materials that are not a natural part of the fish diet. Maintaining antigen stability in oral vaccines is especially challenging under high temperature and high humidity conditions that are common in many countries in Asia and the tropics. Accordingly, there remains a need for improved approaches for the vaccination of fish and crustaceans in aquatic environments.

These challenges can be overcome by genetic engineering of microalgae to lock the vaccine inside the biomass. Microalgae are the basis of all aquatic food chains and are a vital component in efficient, sustainable and profitable aquaculture all over the world. Microalgae is a natural part of the fish diet, and an essential dietary element in the early development of shrimp and other fin-fish. The microalgal oral vaccines can be mixed with fishmeal and fed to the fish, mimicking the natural feeding process. The natural digestion process of the fish unlocks the vaccine/therapeutics proteins and triggers an immune response. In addition, because the vaccine is inside the microalgae chloroplast, it is protected by a rigid cell wall and is stable in harsh environmental conditions, extending the product's shelf life. Such an approach is sustainable, user friendly for fish farmers, and cost effective. However, microalgae being the smallest plant requires sunlight as a source of energy. Hence, they are often grown in photobioreactors. While, photobioreactors are effective systems for manufacturing microalgae. They are often not an economical viable process for manufacturing therapeutics since photobioreactors rely on sunlight, it is not possible to achieve batch to batch consistency, sunlight is not available in all geographic regions and loss of productivity due to seasonal variations. Therefore, microalgae based oral delivery platform technology have poor yield and productivity. In addition, the technology has challenges with regulatory approval due to lack of batch to batch consistency.

BRIEF SUMMARY OF THE INVENTION

The invention addresses the need for improved methods for the vaccination of aquatic animals and provides related benefits. This is accomplished, at least in part, by nucleic constructs having a heterologous nucleotide sequence operably linked to a constitutively active promoter, which is configured for integration into the chloroplast genome of a microalgal host cell, for the production of therapeutics useful in the treatment of diseases that affect aquatic animals. The invention also provides host cells transformed with the constructs and a biomass of transformed host cells isolated from culture. The microalgal oral vaccines can be mixed with fishmeal and fed to the fish, mimicking the natural feeding process. The natural digestion process of the fish unlocks the vaccine and triggers an immune response. In addition, because the vaccine is inside the microalgae chloroplast, it is protected by a rigid cell wall and is stable in harsh environmental conditions, extending the product's shelf life. Such an approach is sustainable, user friendly for fish farmers, and cost effective.

In furtherance of the above, in one aspect of the invention, a nucleic acid construct is provided, which includes a heterologous nucleotide sequence operably linked to a constitutively active promoter; a 5' recombination sequence at a 5' end of the construct and a 3' recombination sequence at a 3' end of the construct, wherein the recombination sequences are configured for homologous recombination into a genome of a microalgal host cell.

In some embodiments, the heterologous nucleotide sequence is a DNA sequence including a sense sequence joined to an antisense sequence by a linker sequence configured to form a loop structure after transcription. In still further embodiments, transcription of the heterologous nucleotide sequence produces a double stranded interfering RNA (dsRNAi) useful in the therapeutic or prophylactic treatment of a disease suffered by aquatic animals. In still further embodiments, the dsRNA is selected from the group consisting of (but not limited to) interfering RNAs for White Spot Syndrome Virus (silencing VP28, VP26, VP24, VP22, VP11, VP15, VP19, VP15, VP26, VP32, VP37, VP38, VP38A, VP39, VP39B, VP41, VP41A, VP68, VP281, VP292, VP466, VP664), Yellow Head Virus (silencing YHV helicase, polymerase, protease, gp116, gp64), Early Mortality Syndrome (silencing PirA and PirB), and Taura Syndrome Virus (silencing CP1, CP2, and CP3).

Transcription of the heterologous nucleotide sequence is by way of a constitutively active promoter having a high transcription efficiency. In some embodiments, the promoter is a T7 promoter. In other embodiments, the promoter can be a T5 or T4 promoter. In yet other embodiments, the promoter sequences can be obtained from endogenous chloroplast genes, which are all originally derived from and evolved from endosymbiotic bacteria. These promoters have binding affinity to sigma70-like transcription initiation factors, which are common in bacteria like *E. coli*. These can include the promoter regions of the 16S ribosomal subunit, the 5S ribosomal subunit, chloroplast tRNA promoters, and the promoter regions of constitutively active genes like rbcL, atpA, and atpB.

In other embodiments, the nucleic acid construct includes a DNA nucleotide sequence encoding a polypeptide; a bacterial 5' untranslated region (5'UTR) between the 5' recombination sequence and the promoter; and an endogenous 3' untranslated region (3'UTR) between the 3' recombination sequence and the nucleotide sequence encoding the polypeptide. Preferably, the polypeptide is a therapeutic or prophylactic agent for a disease found in aquatic animals.

In some embodiments the polypeptide is a therapeutic agent against Viral Nervous Necrosis. In such embodiments, an immunogenic antigen from the Nervous Necrosis Virus capsid protein (VP) can be encoded by the heterologous nucleotide sequence to provide a vaccine against the disease in several different species of fish, including (but not limited to) warm water species like tilapia and grouper. Other diseases for which recombinant antigens can be produced to illicit an immune response include (but are not limited to) Salmonid Rickettsial Septicemia (antigenic peptides ospA, rOmpB), Infection Pancreatic Necrosis (antigenic peptides for capsid proteins and polymerases, VP1, VP2, VP4, VP5), Viral Nervous Necrosis (antigenic peptides for capsid proteins and polymerases, alpha, and NNV VP), streptococcus agalactiae infection (antigenic peptide GapA).

The untranslated regions increase expression of the polypeptide during translation. In some embodiments, the 5'UTR is a 5'UTR selected from one or more of the group consisting of 16SrRNA, fpsbA, psaA, rbcL, atpA, atpB, and rps16. In some embodiments, the 5'UTR contains several duplicated ribosomal binding sites to increase expression of the polypeptide.

In another related aspect of the invention a vector is provided, which includes a nucleic acid construct as set forth herein. In still another related aspect of the invention, a host cell is provided, which is transformed with a nucleic acid construct as provided herein or a vector as set provided herein.

In still another related aspect of the invention a biomass is provided, which includes a host cell transformed with a nucleic acid construct, that is isolated from culture, in a dried form and optionally lyophilized.

BRIEF DESCRIPTION OF THE DRAWINGS

FIG. 3 depicts an exemplary sequence of VP28 sense DNA joined to VP28 antisense DNA by linker DNA (SEQ ID NO: 1), where the underlined portions are the VP28 sense and antisense sequences and the bold sequences are the linker.

FIG. 4 is a table of viral proteins that can be targeted using the nucleic acid constructs according to the invention.

FIG. 7 depicts a synthetic construct (SEQ ID NO: 2) formed by fusing the 463bp *Chlorella* 16S rrn promoter to the T7g10 5'UTR.

FIG. 8 depicts a 367 bp sequence from Chlorella vulgaris, useful as a 3'UTR (SEQ ID NO: 29).

FIG. 9 is a table showing a list of chloroplast promoter sequences which have homology to prokaryotic bacterial promoter elements for use in the invention.

FIG. 12 is an annotated photograph of an agarose gel confirming the presence of the nucleic acid construct with VP28 insert in Colony #6 and a vector map depicting the site of restriction for testing.

DETAILED DESCRIPTION OF PREFERRED EMBODIMENTS

Figure 1:
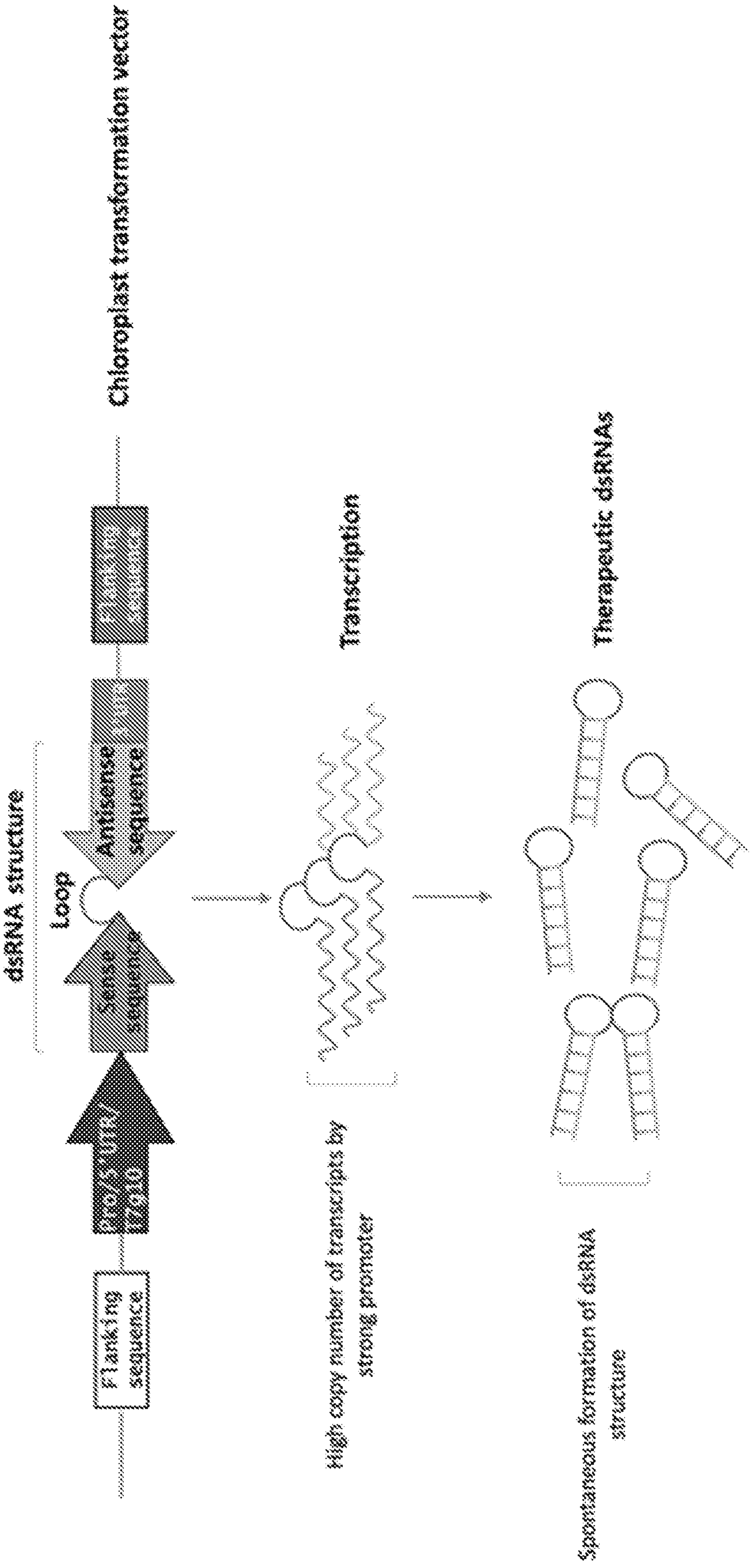
FIG. 1 is a schematic depicting an exemplary DNA nucleic acid construct joined to a chloroplast transformation vector, and the formation of therapeutic double stranded RNA (dsRNA) structures from transcribing the construct in microalgae.

The invention provides DNA constructs for the production of recombinant proteins. In particular, the DNA constructs are adapted for integration into microalgae and result in high protein yield, at least in part due to constitutive promoters that allow the microalgae to be grown/manufactured by fermentation technology. Therefore, unlike conventional microalgal systems, the constructs herein do not require sunlight. The fact, that the DNA constructs allow protein expression in the absence of light, the manufacturing process is commercially feasible for large and economic scale, provides batch to batch consistency and is independent of seasonal variation.

It is to be understood that the foregoing general description and the following detailed description are exemplary and explanatory only and are not restrictive of any subject matter claimed. It is to be understood that the methods and compositions described herein are not limited to the particular methodology, protocols, cell lines, constructs, and reagents described herein as such may vary.

A. Definitions

Unless defined otherwise, all technical and scientific terms used herein have the same meaning as is commonly understood to which the claimed subject matter belongs. In the event that there is a plurality of definitions for terms herein, those in this section prevail. All patents, patent applications, publications and published nucleotide and amino acid sequences (e.g., sequences available in GenBank or other databases) referred to herein are incorporated by reference.

It is also to be understood that the terminology used herein is for the purpose of describing particular embodiments only, and is not intended to limit the scope of the methods, compounds, compositions described herein.

The term "heterologous" as used herein refers to a nucleotide sequence or a polypeptide that is non-naturally occurring in the host cell that is to be transformed or transfected with the nucleic acid construct. A heterologous nucleotide sequence may augment the expression of a protein of interest from an endogenous equivalent gene, i.e. one which normally performs the same or a similar function. A heterologous nucleic acid may comprise a coding sequence of, or be derived from viral origin (e.g. a viral envelope protein).

The term "interfering RNA" or "RNAi" as used herein refers to an RNA molecule that binds a messenger RNA (mRNA) molecule to interfere with or decrease translation of the mRNA into protein. The invention includes the formation of double stranded RNA (dsRNA) to silence or reduce the expression of viral disease.

The term "promoter," as used herein refers to a recognition site on a strand of DNA to which RNA polymerase binds. The promoter is usually a DNA fragment of about 100 to about 200 base pairs. The promoter forms an "initiation complex" with RNA polymerase to initiate and drive transcriptional activity. The complex can be modified by activating sequences termed "enhancers." A "constitutively active promoter" is an unregulated promoter than remains "on."

The term "operably linked" as used herein refers to joined as part of the same nucleic acid molecule, suitably positioned and oriented for transcription to be initiated from the promoter.

The term "recombination sequence" as used herein refers to a nucleic acid sequence configured to undergo homologous recombination with genomic DNA of a host cell, preferably a microalgal cell. Recombination sequences are positioned at opposing ends of constructs that are to be incorporated into the genome of the host cell for homologous recombination.

The term "homologous recombination" as used herein refers to a reaction between any pair of DNA sequences having a similar sequence of nucleotides (homologous sequences), where the two sequences interact (recombine) to form a new recombinant DNA species. The frequency of homologous recombination increases as the length of the shared nucleotide DNA sequences increases, and is higher with linearized plasmid molecules than with circularized plasmid molecules. Homologous recombination can occur between two DNA sequences that are less than identical, but the recombination frequency declines as the divergence between the two sequences increases. The term "configured for homologous recombination into a genome" means the 5' and 3' recombination sequences of the construct are sufficiently similar to nucleic acid sequences within the receiving genome that a homologous recombination event can occur.

The terms "5'" and "3'" as used herein refer to the relative position along a DNA molecule, where 5' is conventionally upstream and 3' is conventionally downstream in regards to the direction of transcription.

The term "linker" as used herein refers to DNA which contains the recognition site for a specific restriction endonuclease. Linkers may be ligated to the ends of DNA fragments prepared by cleavage with some other enzyme. In particular, the linker provides a recognition site for inserting the heterologous nucleic acid, which contains a specific nucleic sequence to be transcribed and potentially translated. When configured to link sense to antisense nucleic acid strands, the linker is configured to avoid complementary binding to each strand so that the linker forms a loop connecting a double stranded molecule characterized by its sense and antisense strand. This recognition site is preferably an endonuclease restriction site, such as, but not limited to EcoR1, HindIII, XhoI, NheI, Sfi-I, and others known in the art to which the invention belongs.

The term "sense sequence" as used herein refers to a strand of DNA that has a same sequence as a corresponding mRNA, and the term "antisense sequence" as used herein refers to an antisense strand of DNA, which acts as template during transcription, and can undergo translation into a protein. The antisense strand is therefore responsible for the RNA that is later translated to protein, while the sense strand possesses a nearly identical makeup to that of the mRNA. The sense and antisense sequences are complementary and can be aligned in opposite directions on a same DNA strand as heterologous nucleotides to cause complementary binding after transcription. Complementary binding can be encourage by way of a linker that links the two sequences.

The term "untranslated region" as used herein refers to either of two sections, one on each side of a coding sequence on a strand of mRNA. If it is found on the 5' side, it is called the 5'UTR (or leader sequence), or if it is found on the 3' side, it is called the 3'UTR (or trailer sequence). The 5' UTR is upstream from the coding sequence. Within the 5' UTR is a sequence that is recognized by the ribosome which allows the ribosome to bind and initiate translation. The 5' UTR in the instant invention acts as an enhancer to increase translation. A "bacterial untranslated region" does not require the untranslated region be excised from bacterial but instead refers to a nucleic acid sequence that is also found in bacteria or is a nucleic acid sequence having sufficient sequence similarity to a sequence found in bacteria that would result in a same effect in bacteria, such as increasing translation.

The term "therapeutically active" as used herein refers to the ability to achieve an improvement in an animal suffering from a disease or reducing a risk of developing a disease. Nonlimiting examples of such improvements include increased survival rate, more rapid recovery, or improvement or elimination of symptoms, and other indicators as appropriate determining measures by those skilled in the art.

The terms "effective amount" or "therapeutically effective amount," refer to a sufficient amount of recombinant microalgae or therapeutic agent described herein administered which will relieve to some extent one or more of the symptoms of the disease, disorder or condition being treated.

The term "multicloning site" as used herein refers to a sequence of DNA having more than two endonuclease restriction sites.

The term "vector" as used herein refers to a nucleic acid molecule capable of transporting another nucleic acid to which it has been linked. One type of vector is a "plasmid", which refers to a circular double stranded DNA loop into which additional DNA segments may be ligated.

The term "expression cassette" as used herein refers to the genetic material of interest which codes for a protein or RNA. The expression cassette is positionally and sequentially oriented within the vector such that the nucleic acid in the cassette can be transcribed into RNA, and when necessary, translated into a protein in the transformed cell. Preferably, the cassette has 3' and 5' ends adapted for ready insertion into a vector, e.g., it has restriction endonuclease sites at each end.

The term "amino acid" as used herein refers to the molecules composed of terminal amine and carboxylic acid functional groups with a carbon atom between the terminal amine and carboxylic acid functional groups sometimes containing a side chain functional group attached to the carbon atom (e.g. a methoxy functional group, which forms the amino acid serine). Typically, amino acids are classified as natural and non-natural. Examples of natural amino acids include glycine, alanine, valine, leucine, isoleucine, proline, phenylananine, tyrosine, tryptophan, serine, threonine, cysteine, methionine, asparagine, glutamine, lysine, arginine, histidine, aspartate, and glutamate, among others. Examples of non-natural amino acids include L-3,4-dihydroxyphenylalanine, 2-aminobutyric acid, dehydralanine, g-carboxyglutamic acid, carnitine, gamma-aminobutyric acid, hydroxyproline, and selenomethionine, among others. In the context of this specification it should be appreciated that the amino acids may be the L- optical isomer or the D -optical isomer.

B. Microalgae as a Host for Therapeutic Agents

The invention provides nucleic acid constructs for integration into the genome of microalgae for the formation of therapeutic agents. Microalgae have the potential to be an extremely effective oral delivery system for vaccines and therapeutics because they possess several key properties that make them a robust platform. Therapeutic nucleotides expressed within the microalgal biomass are protected within the rigid cell wall of the microalga, allowing the therapeutic or vaccine to remain heat and temperature-stable for up to 1.5 years, and allows the therapeutic molecules to survive the harsh acidic environment of the stomach and be absorbed by aquatic organisms (1). Although the technology is promising, the realization of its potential as a viable platform technology has remained a challenge due to issues with commercial scale-up. Virtually all previous DNA expression vectors for use in microalgae describe the use of photobioreactors or sunlight to grow microalgal therapeutics. Here, we present the first DNA expression vector built specifically for microalgal chloroplast fermentation.

Among the species of microalgae that can be used as a host for expression of therapeutic agents in the invention include, but are not limited to *Chloroficeae, Haematococcus pluvialis*, Bacillariophyceae, Dinophyceae, *Scenedesmu* sp, *Chlorella* sp., *Nannochloropris* sp, Diatoms, *Phaeodactylum tricornutum, Crypthecodinium* sp. and *Galdieria* sp. Preferably, the micralgae is a species that can be be cultured on a large scale using fermentation. In some embodiments, the species is *Chlorella vulgaris*, which may be chosen for its high heterotrophic growth rate, and its ability to rapidly assimilate a variety of carbon sources such as glucose, galactose, and acetate(2).

Microalgae can be transformed with the constructs using conventional techniques known in the art, such as glass bead-assisted transformation, PEG-mediated transformation, micro-injection, particle gun-mediated transformation, electroporation, CRRISPR/CAS9 and shuttle protein-mediated plastid engineering. Furthermore the recombinant microalgae are amenable to high density growth using fermentation.

The therapeutic agents can be conveniently stored by freeze drying the recombinant microalgae itself. When used to deliver therapeutics to fish, crustaceans and other animals that naturally feed on microalgae, the recombinant microalgae can be supplied for natural feeding. The recombinant microalgae and therapeutic agents provide oral vaccination of fish (grouper, pompano, bass, mullet, seabass, snapper, barramundi, cod, catfish, cuppy, eel, cobia, tilapia, founder, turbot, puffer, striped jack, senegalese sole, sea bream) against diseases such as nervous necrosis viruses (NNV).

In some embodiments, the microalgae is combined with other carriers or agents that facilitate delivery or with other compounds for improved therapeutic effect. When orally delivered, the microalgae can be formulated with an adjuvant to boost immune response. Among these include poly I:C (recombinant dsRNA), Flagellin fusion proteins, imiquimods, CpG, saponins, squalines, mineral oils and surfactants.

C. Nucleic Acid Constructs

The invention provides nucleic acid constructs having a heterologous nucleotide sequence operably linked to a constitutively active promoter to form an expression cassette; and flanking recombination sequences configured for homologous recombination into the genome of a microalgal host cell. Upon homologous recombination, the recombinant host cell itself transcribes the heterologous nucleotide to RNA. In some embodiments the RNA is embodied as double stranded RNA (dsRNA) and is provided as a therapeutic agent. In such instances, the dsRNA may act as interfering RNA to interfere with translation of viral proteins. Such an embodiment is particularly useful to combat a variety of diseases that occur in aquatic populations, such as fish farms, prawn farms, and others. In other embodiments, the RNA is translated into a protein and provided as a therapeutic agent, which can be delivered by administering the recombinant microalgae itself or isolating the therapeutic agent and forming a therapeutically acceptable formulation for administration. In these embodiments, the invention is particularly useful in the formation of a vaccine against disease found in aquatic environments, such as fish farms, prawn farms, and others.

As depicted in FIG. 1, in some embodiments, the invention provides DNA constructs for the improved production of dsRNA for use as a therapeutic agent. In such embodiments, the heterologous nucleotide sequence can be embodied as a sense sequence joined to an antisense sequence by a linker, which upon transcription loops to permit complementary binding of RNA strands to form the double stranded RNA molecule.

White Spot Syndrome is a virulent disease that infects farmed crustaceans and is responsible for at least 1 billion USD of economic damage to the aquaculture industry each year by some conservative estimates (3). RNA interference has shown to be a promising technology to treat and prevent the pathogenesis of this economically devastating disease (4). One of the major setbacks of using RNA interference for treating white spot syndrome is the lack of an effective and economically viable platform to express and deliver the therapeutic RNAs. The nucleic acid constructs and approach solve this problem by providing a nucleic acid construct that can be integrated into the genome of a microalgal host cell and configured to produce high concentration of therapeutic dsRNA using heterotrophic fermentation.

Figure 2:
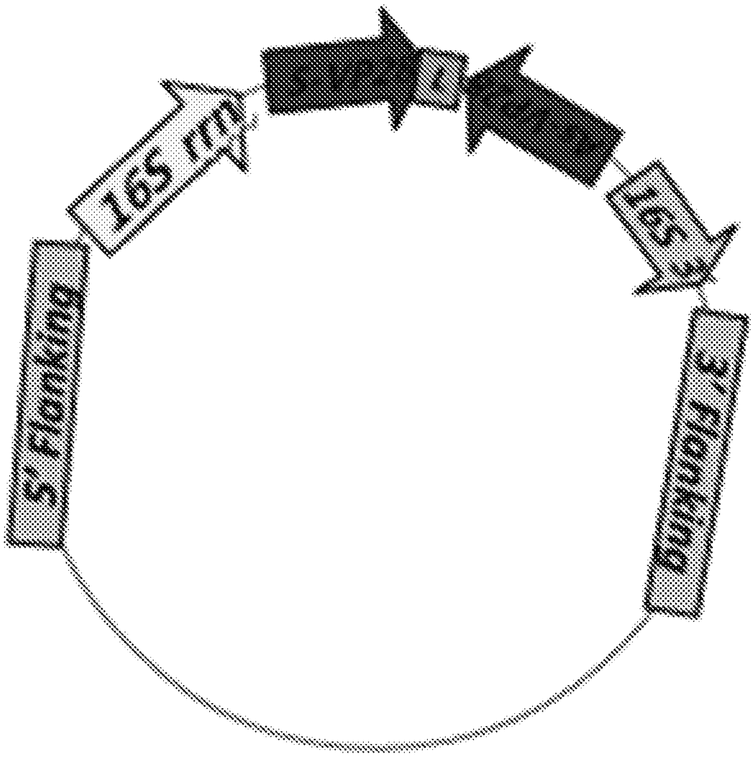
FIG. 2 is a schematic depicting a DNA nucleic acid construct incorporated into a chloroplast transformation vector and configured to undergo homologous recombination in microalgae to produce VP28 dsRNA at high copy number for the treatment of white spot in aquatic animals.

In furtherance of the above, FIG. 2 is a schematic depicting a nucleic acid construct inserted into a chloroplast vector for the production of VP28 in the formation of a dsRNA for the treatment of aquatic animals against white spot. In addition, FIG. 3 is a DNA sequence of the VP28 sense and antisense sequences joined by a linker (SEQ ID NO: 1), where the VP28 sequences are underlined and the linker is highlighted by bold typeface. Similarly, other viral proteins can also be targeted using the approaches herein. Among those include the viral proteins provided in FIG. 4, where the heterologous nucleotide sequence is configured to bind the viral protein encoded RNA relying at least in part on sequence complementarity. Configuring heterologous nucleotide sequences to bind viral encoded RNA can be accomplished using conventional molecular biology tools known in the art, such as those that reverse translate polypeptide sequences and reverse transcribe RNA sequences.

Figure 5:
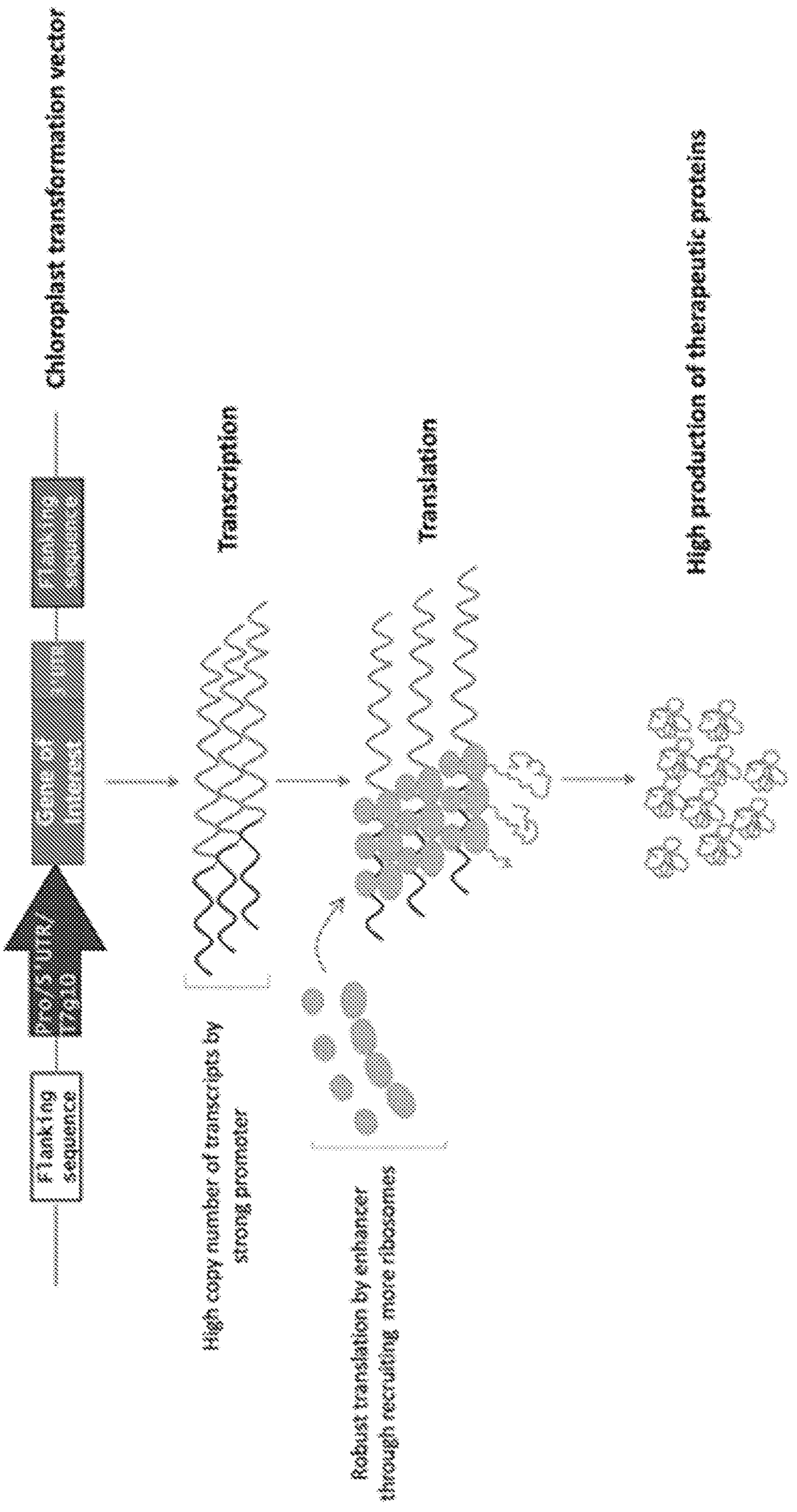
FIG. 5 is a schematic depicting an exemplary nucleic acid construct joined to a chloroplast transformation vector, and the resulting high production of therapeutic proteins due to a high copy number of mRNA transcripts from a strong promoter and robust translation by 5'UTR enhancers.

As depicted generally in FIG. 5, in some embodiments the production of a therapeutic protein is desired. In such embodiments, the heterologous nucleotide sequence can be a DNA sequence encoding the therapeutic polypeptide or protein operably connected to a promoter. Determining a DNA sequence that encodes a therapeutic polypeptide or protein can be performed using conventional molecular biology tools known in the art, such as those that reverse translate polypeptide sequences and reverse transcribe RNA sequences.

In some embodiments the heterologous nucleotide for expression as a polypeptide is a therapeutic agent against Viral Nervous Necrosis. In such embodiments, an immunogenic antigen from the Nervous Necrosis Virus capsid protein (VP) can be encoded by the heterologous nucleotide sequence to provide a vaccine against the disease in several different species of fish, including (but not limited to) warm water species like tilapia and grouper. Other diseases for which recombinant antigens can be produced to illicit an immune response include (but are not limited to) Salmonid Rickettsial Septicemia (antigenic peptides ospA, rOmpB), Infection Pancreatic Necrosis (antigenic peptides for capsid proteins and polymerases, VP1, VP2, VP4, VP5), Viral Nervous Necrosis (antigenic peptides for capsid proteins and polymerases, alpha, and NNV VP), streptococcus agalactiae infection (antigenic peptide GapA).

Among the antigens that can be targeted for heterologous nucleotide sequence are provided in TABLE 1.

TABLE 1

Antigens for encoding in the heterologous sequence

| Bacterial/Viral Disease | Antigen Name | Uniprot/NCBI Accession Number |
|---|---|---|
| Nervous Necrosis Virus | Viral Capsid Protein (CP) | UniProtKB - A0A0F7GYD4 |
| Nervous Necrosis Virus | RNA-directed RNA polymerase | UniProtKB - Q993M1 |
| Salmonid Rickettsial Septicimia | lipoprotein antigen (ospA) | Genbank (No. CP013821.1) |
| Salmonid Rickettsial Septicimia | Outer membrane protein B (rompB) | UniProtKB - Q9KKA3 |
| Infectious Pancreatic Necrosis Virus | RNA Directed RNA Polymerase (VP1) | UniProtKB - P22173 |
| Infectious Pancreatic Necrosis Virus | Viral Protein 2 (VP2) | UniProtKB - Q703G9 |
| Infectious Pancreatic Necrosis Virus | Viral Protein 4 (VP4) | UniProtKB - M9VYM2 |
| Infectious Pancreatic Necrosis Virus | Viral Capsid Protein 5 (VP5) | UniProtKB - Q6U2P6 |
| *Streptococcus agalactiae* | glyceraldehyde-phosphate dehydrogenase protein (GapA) | GenBank (No. AFS46447) |

The promoter drives transcription of the heterologous nucleotide sequence. Preferably, the promoter is chosen based on how well it binds with Plastid Encoded Polymerases (PEPs) and with sigma70-like transcription factors so that the heterologous nucleotide sequence can transcribed at high copy number. These two measurements are strong indicators for how efficiently a gene is transcribed into RNA.

Figure 6:
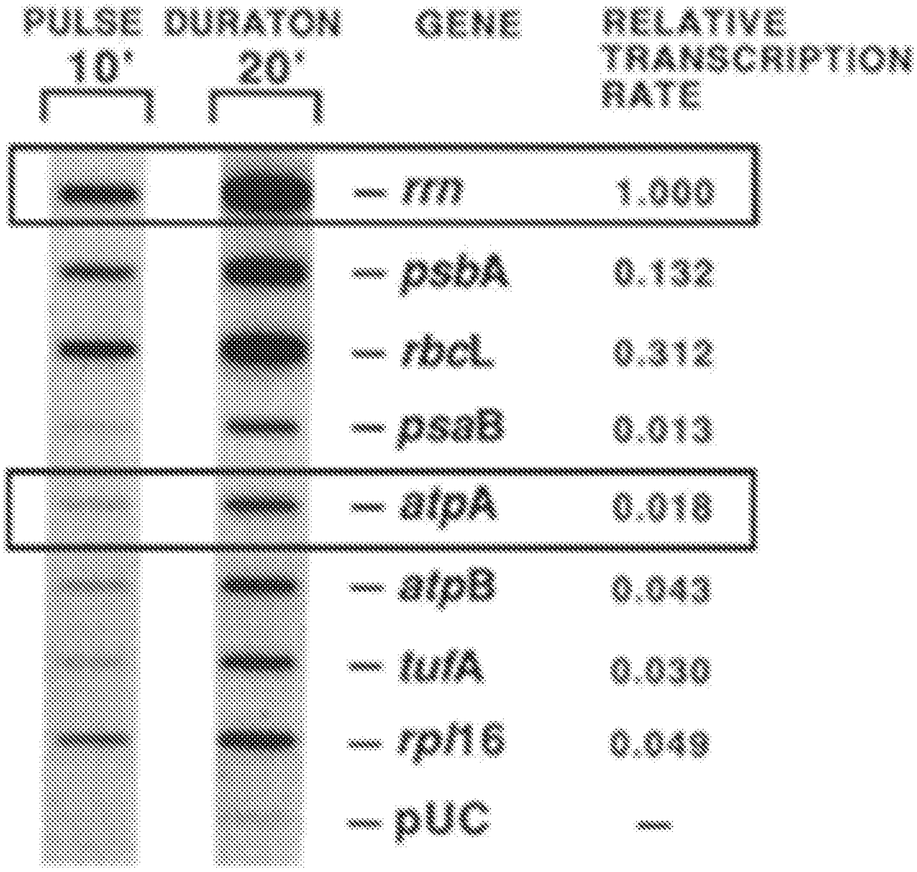
FIG. 6 is a photograph depicting results from northern blotting with corresponding calculated relative transcription rates of chloroplast mRNAs in *C. reinhartii* cells using the promoters rrn, psbA, rbcL, psaB, atpA, atpB, tufA, rp/16, and pUC.

In contrast to conventional microalgal systems, the nucleic acid construct makes use of a strong, constitutive promoter sequence whose activity is not regulated by light. A plurality of promoters were compared for their efficiency at transcription; the results of which are depicted in FIG. 6. In particular FIG. 6 shows the relative transcription rate of 16S ribosomal rRNA (rrn) is 55 times higher than atpA. Accordingly, in a preferred embodiment, the 16S rrn promoter is provided to drive transcription in the nucleic acid construct. FIG. 7 depicts the 463 bp 16S rrn promoter region (shown in bold) upstream of 16S rrn in Chlorella vulgaris (SEQ ID NO: 2).

In other embodiments, promoters having lesser efficiency than the 16S rrn promoter may be used; however, in embodiments where protein expression is desired, the invention may include further enhancers within the untranslated regions to increase production. As a nonlimiting example, rbcL was shown to also have a higher efficiency than atpA and thus can also be used. The rbcL gene encodes the RuBisCo large subunit to support the dark reactions of photosynthesis and are generally always expressed. One skilled in the art can also use promoters from core housekeeping genes within the chloroplast.

TABLE 2 is depicted in FIG. 9, which provides chloroplast promoter sequences having homology to prokaryotic bacterial promoter elements. These sequences are homologous to promoters in other plants, such as microalgae and can therefore be incorporated into the nucleic acid construct. Note the -10 and -35 bacterial promoter consensus sequences which also appear in these chloroplast promoters (TTGACA and TATAAT) (10). SEQ ID NOS: 1-18 and additional chloroplast promoters for use with the invention may be found in Kung, S. D. and Lin, C. M. (1985) Chloroplast promoters from higher plants. *Nucleic Acids Res,* 13, 7543-7549.

Alignment with chloroplast genome of the green microalga, *Chlamydomonas reinhardtii* shows the same conserved -35 and -10 motifs found in higher plant chloroplasts and bacterial promoters. The same homology is observed in microalgae.

In embodiments where the heterologous nucleotide sequence is to encode a therapeutic protein, the invention preferably includes bacterial untranslated regions to increase translation, thereby increasing protein yield. Most preferably, a bacterial 5'UTR is positioned between the 5' recombination sequence and the promoter and the bacterial 3'UTR is positioned between the 3' recombination sequence and the heterologous nucleotide sequence.

Selection of 5'UTR is based on mRNA structural stability and ribosome binding strength. In one embodiment of the invention, the bacteriophage T7g10 5'UTR/enhancer sequence is used to build a DNA vector to express therapeutic proteins, since it is a highly translationally active 5' UTR regulatory element which has been shown to produce high expression levels in the chloroplasts of higher land plants, and is not downregulated by the presence or absence of light or a particular substrate.

The 5'UTR, when transcribed, has nucleotide elements with homology to conserved prokaryotic ribosomal binding site sequences (typically AGGAGGU a similar variant) which has complementarity to the RNA binding region of the plastid 16S ribosomal RNA sequence.

Other candidate 5'UTR elements include the 5' UTR of psbA, psaA, rbcL, atpA, atpB and rps16. Multiple ribosomal binding sites can also be inserted to increase the rate of translation, increasing the product yield. TABLE 3 provides exemplary 5' UTR sequences for use in the invention.

TABLE 3

5' UTR sequences

| SEQ ID NO: | 5'UTR | Origin | Sequence |
|---|---|---|---|
| 19 | T7g10 | T7 Bacteriophage | GGGAGACCACAACGGTTTCCCaCTAG<br>AAATAATTTTGTTTAACTTTAAGAAGGA<br>GATATACAT |
| | *E. coli* 16S rrn | Bacteria | ACCTCCTTA |
| 20 | rbcL | *Chloralla vulgaris* Chloroplast | gatgaaaaaaagatcaaaaagaaaaaaaagctagag<br>aaaatcaaggtttgaaaaaaaatatttttttcatgccttgat<br>tttctttagaaagagaaaaataatgaatttttcaacagtag<br>aacagaatcaaaagaatttcactcttgtgatactctaaaa<br>aatatgctatactctggtgtaaaacaaaaagacaagaa<br>attacactttttttcgggcagagtgcaagatcgtaaaccat<br>aattttttttaga |
| 21 | psbA | *Chlorella vulgaris* Chloroplast | aaaaattaaaatgtttttcttttttcctaaaaaggagtttttcc<br>caaaattaaaaaaatttaatttgttaggccctactgtaacta<br>aaatctaaatctcagtcaagtaactattaaaataaagatt<br>aaaataaacaaaaaggctactcgatttaaaattaggttttt<br>atattaatttgaaaaactttttttaacaagtaaaaaaagaa<br>gaaaaaatactctaattcttaagattttcaacacataaatt |
| 22 | atpA | *Chlorella vulgaris* Chloroplast | ggtaCttctgaactgcctcctctttgttacaaaactcgacgt<br>tttgccattcatattgtattaactggctttagaattcgtaaaaa<br>gcacaatttgaaaattattcactgcactatgaattgaagaa<br>gttaatcgttgattaagtttttcgcgaacttgttgtaatgccag<br>ttttactaatttttccgcaagttcattttgagctttttgttgctcaa<br>actttaaggtctcctgttggagagtacctaaacgttttatatc<br>ttcttgtgtttggcgaatgaattg |
| 23 | rpoC1 | *Chloralla vulgaris* Chloroplast | gaaaaaaaaacggaatcagaaaagaaagaaatgac<br>aaaaaaatgatttttttcattccatttttttttttagaaaaaaaa<br>acgaaaattaaggcatttatttttttaaggatcaaaaagatt<br>tttttttcaagcctatctttttttttctaaaaaaaaagaagggt<br>ggaacccttcattttctgattccatttttttttttttaagaaagaa<br>aatcttgattttagaactttttttagctctttttttaaattgggctttt<br>gtttgatattcttttgtacaaattaaagaaaacactaaaacc<br>tttccaccctaagt |

TABLE 3-continued

| 5' UTR sequences | | | |
|---|---|---|---|
| SEQ ID NO: | 5'UTR | Origin | Sequence |
| 24 | psaA | *Chlorella vulgaris* Chloroplast | gtttcatttaaacgaaaattgtactgagtgttttaaccaaaa<br>tttaagcacctttgcagatttcgtcatctttcttttttttgaaaaa<br>aaaagaaataaaaagaaaaaaagctgttttaaactgaa<br>tagtaactaaccctttatgcaccagagttctatgggatcct<br>ataacgaaactctcaagttactcttttgtgagtacaatcaa<br>acgcaagactcatatttctgtctagtgattttgtaaatttttgg<br>aactaccaaaaattagaacttttggtttcaaatttcaactttg<br>tcattatttttttgattttcttaaccgctatttttttaaaaatactg<br>tggtaagattttaaaaagataatttcggtaattcaaataa<br>ggagaatttttcgcc |
| 25 | T7g1.3 | Bacteriophage | tacgactcagtatagggacaatgcttaaggtcgctctcta<br>ggagtggccttagtcatttaaccaataggagataaacatt |
| 26 | psbH | *Chlorella vulgaris* Chloroplast | aatttcaagggtagtagaatttttttttactttctgtaacgaga<br>aaactaaaagaaagttttataaattttaaatcattttagttttc<br>gattttaacgtcaatttttttcagactttcttccaattttattatata<br>gtaaattttaaattggaaaaaggttttagttacttctttcgaa<br>aacgcaactaaaagtataaaatgtttttttgaaaacaaaat<br>ttttagtttctttaaagtttttta |

The selection of the 3'UTR is based on structural stability. Generally, the choice of 3'UTR has little effect on the expression of the gene. In most embodiments of the invention, the 3'UTR of rbcL is chosen. In other embodiments, the 3'UTR of 16S rrn of *Chlorella vulgaris* (SEQ ID NO: 27 and shown in FIG. 8 may be use as the 3'UTR. In yet other embodiments, one can use the 3'UTRs of atpA, psA or others. TABLE 4 provides exemplary 3' UTR elements.

TABLE 4

| 3' UTR sequences from *C. vugaris* | | |
|---|---|---|
| SEQ ID NO: | 3'UTR | Sequence |
| 28 | rbcL | ttttcaactaaactgttccagttctaaagaaaattaaggaaaat<br>ccttaattttctttaactttttttcttttttttttcttctttttgatcttttttttttta<br>taaaaaaaagaaaaaggaaaaaaaagatcaaaaaggtc<br>tacttaaaaacataaatgccttgcattt |
| 29 | 16s rrn | ccttttaaaggataaaaaaaccttaagaaaaaacaaagttttt<br>cttaagtactccaatccttctttctttttttattcccattaaattgaat<br>aaaaattaaacgttttcttactttaatgagaatataaattaagat<br>gatttccgtttttttgaaatccagtttttggttttttttttccttcttttttttttt<br>ataaaaaaaaagatcaaaatgaatcaaaaactaatagaa<br>aaaaacggaatttgaagaattgattcatttttttacatgtgcatga<br>gtcactagcttgctttttttagtgcactaacctcttctcca |
| 30 | atpA | aaaagtatgttttattagtaaagtatcagatttatacagagctta<br>ataaaaacagggcccaataaatgaatgggaaaaattttaaa<br>ttatgttttttttactttgatctttttttttagttcttttttttcttttttttttttttga<br>aaaaaaaaagaaaaaaaagaactaaaaaaaaagatca<br>aaagtaaaaaaaacataaccaaaaaataccagcaaagc<br>atgtattttttttaagggttgagatacttagtt |
| 31 | psaA | gaaaaccaggcaaaaaatttcgtttctcttactttaaagaattg<br>gaaaggtttctgattccacaaaaaaaatgcgaagcatttttttta<br>taattcctttttttgctcttcctaaaaaaaaaatgcaaagcattttt<br>ttttaggataatttctgattctttttgatcttttttttttagttctttttgatgt<br>ttttttttttataaaaaaaaaacaaatagaaaaaaaaagaaaa<br>aaaagaagcaaaaaaagatcaaaaaggaaatagtaggc<br>aggtttccaacttaaaaaattaaaagcaaagctt |

The choice of 5' and 3' homologous recombination sites used to integrate the construct into a chloroplast can affect expression. Different regions of the chloroplast genome can have different levels of expression. The most transcriptionally active intergenic spacer regions are used to create the construct. In one embodiment of the invention, homologous recombination sites from the chloroplast of a species of heterotrophic microalga, *Chlorella vulgaris*, are chosen in order to integrate the DNA Expression Cassette into a transcriptionally active intergenic spacer region. This region is located between rbcL and trnS within the chloroplast genome. Other transcriptionally active spacer regions that are generally used for high expression and thus are a target for homologous recombination include include trnI/trnA, rps14/trnG, trnP/rps12.

D. Therapeutic Treatment

In some embodiments the construct is configured to produce a therapeutic agent embodied as a dsRNA configured to interfere with viral DNA. In other embodiments, the therapeutic agent is used as a vaccine for animals, and in particular aquatic animals such as fish and crustaceans. Microalgae provides not only an efficient host for therapeutic production but also provides an effective delivery vehicle, thereby reducing the complexity of the therapeutic formulations themselves.

Whether the therapeutic agent is delivered by freeze dried tablet or powder or whether combined with subsequent agents, the therapeutic agent is provided to the animal population in a therapeutically effective amount or a prophylactically effective amount. It is understood that "an effect amount" can vary from species to species due to variation in metabolism of the microalgae or the therapeutic agent, genetics, composition, age, weight, general condition of the species, the condition being treated, the severity of the condition being treated, and the judgment of those having skill in the treatment of such species.

To demonstrate the bioavailability of orally delivered vaccine antigens expressed in microalgal chloroplasts to fish, codon-optimized green fluorescent protein (GFP, 717bp) was cloned into a chloroplast expression vector as described in Example II.

EXAMPLES

Example I

Construction of a Vector with Expression Cassette for Integrating White Spot Syndrome Virus VP28 dsRNA Coding Sequence Into the Genome of *Chlorella vulgaris*

Figure 10:
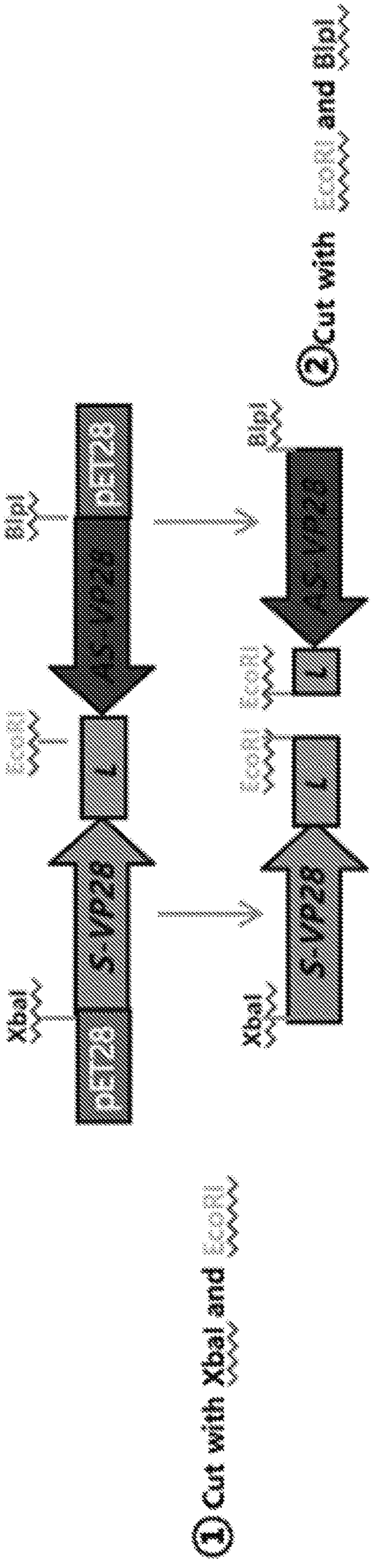
FIG. 10 depicts an overview of the isolation and processing of VP28 encoding sense and antisense DNA for use as a heterologous nucleotide sequence in the nucleic acid construct.
Figure 11:
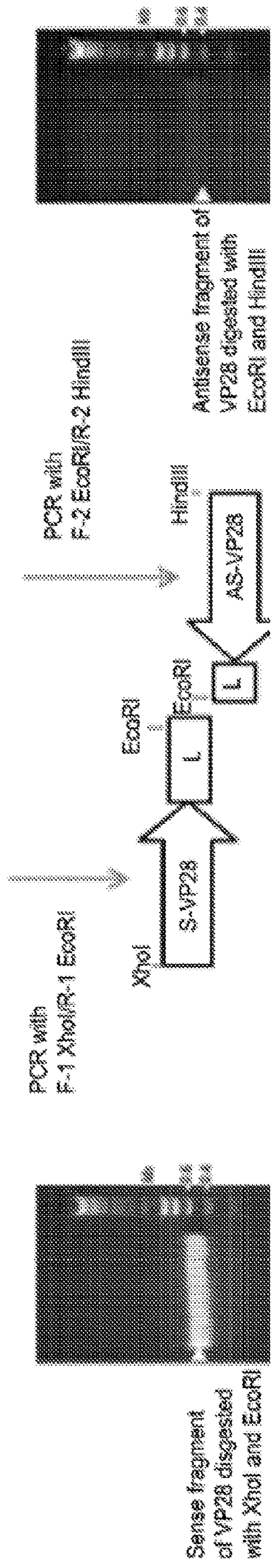
FIG. 11 depicts the amplification of restricted sense and antisense VP28 nucleic acid sequences.

Serving as a DNA vector backbone, pASapI was provided courtesy of MicrosynbiotiX's scientific advisor, Dr. Saul Purton (5). As depicted pictorially in FIG. 10, VP28 dsRNA coding sequence with linker (SEQ ID NO: 1) was synthesized then cut with the restriction enzymes XbaI, EcoRI, and BlpI, to produce two digested VP28 sense and antisense fragments with 5' and 3' overhangs. As shown in FIG. 11, the DNA fragments were amplified using a forward primer SEQ ID NO: 32 and reverse primer SEQ ID NO. 33 to create the appropriate overhangs for the VP28 sense fragment, while another set of primers, Forward Primer SEQ ID NO: 34 and Reverse Primer SEQ ID NO: 35 were used to create the appropriate overhangs for the VP28 antisense fragment.

TABLE 5

Primers for VP28 fragment amplification

| SEQ ID NO: | Primer | Sequence |
|---|---|---|
| 32 | VP28 sense forward | TAAAATTCTCGAGATGGATCTTTCTTTCACT CTTTCGGTC |
| 33 | VP28 sense reverse | CCGAGTAAaagggcgaattcgcccctt |
| 34 | VP28 antisense forward | CCGAGTAAaagggcgaattcgcccctt |
| 35 | VP28 antisense reverse | gagtacaagcttATGGATCTTTCTTTCACTCTTT CGG |

The sense and antisense fragments, with complementary overhangs within the linker region, were ligated together using T4 DNA Ligase to produce the palindromic dsRNA gene sequence with restriction sites XhoI and HindIII. The recipient vector (pASapI) was then cut with restriction enzymes XhoI and HindIII to create complementary overhangs. The fragment was then ligated into the pASapI vector.

Cloning of chlorella 16S rrn promoter into DNA Expression Cassette. The chlorella 16S rrn promoter (SEQ ID NO: 36) was synthesized using Thermofisher Gene Art Service and cut using restriction enzymes MluI and XhoI. The same restriction enzymes were also employed to cleave the existing atpA promoter and its 5'UTR from the DNA backbone (pASapI). T4 DNA ligase was then used to assemble the restricted chlorella 16S rrn into the DNA backbone.

TABLE 6

| Synthetic *Chorella* 16S rrn promoter region | | |
|---|---|---|
| SEQ ID NO: | Description | Sequence |
| 36 | Synthetic *Chlorella* 16S rrn promoter prior to restriction | taaagaaaagtgagctattaacgcgtATCAAAGTTAAATT<br>CGTAAATTTTAACTTTGATTCTTCTGGAAGTGC<br>AACTACTTTCCGTTTAGCTGGTTGAAATCTTTA<br>GTATAAATTTTTTTTTAAGCAAAAAATTTAATTT<br>AACTATGATAAATTTAAAAATTAAAGCAAGGAA<br>AAAAAGAAGAGAGAGGAAGACTGGTTTGACTT<br>TTTTTTTATTAAAGATACATTACTAAGTGTGAAA<br>ACAaagcttgtactcaagctcgtaacg |

Replacement of pASapI flanking regions for homologous recombination. Lastly, the 5' and 3' recombination sequences (SEQ ID NOS: 37, 38) were amplified from the chlorella genome and cloned into the Expression vector. The 5' Recombination site (SEQ ID NO: 37) was amplified from chlorella genomic DNA using Forward Primer containing Pcl1 cut site SEQ ID NO: 39 and Reverse Primer containing the Mlu1 cut site SEQ ID NO: 40. The resulting PCR product and the pASapI backbone were then digested with Mlu1 and pcl1, and the overhangs of the insert and the template were joined together using T4 DNA ligase. A similar procedure was employed for the 3' Recombination site (SEQ ID NO: 38), using Forward Primer containing Afe1 restriction site (SEQ ID NO: 41) and a Reverse Primer with restriction site KasI (SEQ ID NO: 42) to amplify the desired region from chlorella vulgaris genomic DNA. The fragment and the insert (pASapI) were both digested with Afe1 and KasI, and the complementary overhangs were joined together using T4 DNA ligase.

TABLE 7

| Insertion of recombination sequences | | |
|---|---|---|
| SEQ ID NO: | Description | Sequence |
| 37 | *Chlorella vulgaris* 5' Recombination Region | ATAAAAAAAAGAAAAAGGAAAAAAAAAGATCAAAA<br>AGGTCTACTTAAAAACATAAATGCCTTGCATTTA<br>TGTTTTTAAGGATAAAAAATATTTTTGGCCGTCT<br>TTCTTTTCTTAAGCTTTTTTTTCAAAAGCTTAAGA<br>AAAGAAAAGATTTTCCTTTATTTTTTTTAGAACCG<br>GAACAAACTTTTGAAAAAAAATTTACTTTTTTTTC<br>ATCAGTCCTCCATTGAAAATGGAGAGTCCCCTT<br>CTTTTTTTTTATAAAAAAAAGAATGAAAAGAAATG<br>CTTTGTATTTCTTTTCTTTAGGAAAAAATAAAATT<br>TTTTCATTTTAACTGATACTAAAATTCGTTTCTTT<br>TTTTTGTGTAATAAAATAAAAAAGAAATAAATAAC<br>TGAACCTAGATATGGCAAAAAAAAGCATGATTG<br>AGCGTGATAGAAAACGCGCTCGTTTAATTACTA<br>AATATGCAGCAAAACGAAAAAATCTCCTCGTAG<br>AAATTAAAACAGCAACTTCTTTAGAAGACAAATT<br>CAATTTACATAGAAAATTGCAACAACTACCAAGA<br>AATAGTGCACCAGTTCGATCTCATAATCGTTGTA<br>CAATTACCGGTCGGCCCAGAGGATATTTTAGAG<br>ACTTCGGCTTATCCCGCCATGTTTTACGCGAAT<br>ATGCTTTACAAGGTTTTTTACCTGGTGTGGTAAA<br>AGCTAGTTGGTAAAAAAACTGTAGTTGACCTATT<br>GACTTTTGATTTCCGTTCTTGTCTTTTCTTTTTGA<br>GCTTTTTTTTATAAAAAAAAAAGAAAAAAAAGCT<br>CAAAAAGAAAAACTACACATTATTAAAGCGTCGC<br>GATCTGGGTATCAGAAACAAAAGCGACATGGTG<br>ATTACATAATTTTAAAGGAAAGCTACATGGTGAT<br>TACATGATTTTAAAGGAAAATTACATAGTGATTA<br>CATAACGTTTTTAGCGAATAAACCTTGCCAATAC<br>AGCATTTTTTTCTTTTTTTTTTTTTTTAATGTGATA<br>TTTAAGTCGTTTAATTTTTCAACACGTTTTTTTA<br>ACAACTTTCGAAATAACAACTTTAACCAACTTGT<br>TTTTAGCCTTACTTAGTTTCAATCAAGAAGTTGG<br>TTTTGAAA |
| 38 | *Chlorella vulgaris* 3' Recombination Region | TCCTTGTTACGGTGGATTTTTAGCTATTGCGCTT<br>TTTCCTTTTTTTTAGTATAATTTTTATTACCTTTTA<br>ACAAGCCTGCTTAGCTCAGTTGGTTAGAGCATC<br>CGTCTCATACGCGGAATGTCACTAGTTCGAATC<br>TAGTAGCAGGCACCATAATTTCGCGGGTATAGC<br>TCAGTGGTAGAGCGGCACCTTGCCAAGGTGCA<br>TGTCGCGCGTTCGACTCGCGTTACCCGCTTATT<br>TTATTTTTTCTATTTAAGTTTTTTCATAAAATCTAA<br>AATTAAAAAGAGTCTATTTAATCCAGTTTTTTGGT<br>TCGAATAGTTTTTCGTTTCTTTTTTTTCAAAAAAAA<br>AAAAGAATGAAAAACTCAAAAAACAAAAACGGG<br>TTCCACCCTTAAAAAAAATGCTGTGCATTTTTTT |

TABLE 7-continued

| Insertion of recombination sequences | | |
|---|---|---|
| SEQ ID NO: | Description | Sequence |
| | | AAGTAAACCCAATGCTTTTTTTTTATAAAAAAAAA<br>GAATGAAAAGAAATTCTTTTTTTTTCATGCCTTTA<br>TTTTCTTTAGAACCGAAAATCAAAGAAAATTTTCT<br>TTTATAAATTAAATCGTTTCTATCTTTTTTTTTCTA<br>AAAAAAAAAGAAGGAAAAAAAAATACTTTTTTCAA<br>AGTTATTACGGAATATGTTAAATCGAGGGTGAC<br>GGGACTCGAACCCGCAACTTCCACCGTGACAG<br>GGTGGTGCTCTGACCAATTGAACTACACCCCCT<br>CGATATGGATTTATCATATCACACATCTTTTTTTT<br>AATGTAGAGCTAGCTGTCAGTTCCAGTACAAATT<br>GTCTATTTTATTTATTTTCAAAAGGAGATAAATCT<br>GTCTTTTAATAAGTTTATAGCTGAATAAAAAATTT<br>TTCTCTTACGAAAATAAATGCAAAGCACTTATTT<br>CCTGATTTCGTTTTTTAAATTGAATAGTTTTTTTT<br>CTTTTTTTCAAAAAAAGAAAGAAAAACTCCAGGT<br>TAAAAAACGGCTTTGAAGCGACTTCCGTTTTTTT<br>ATTCAATGAGTTTTTCTTTAGAAAAACTTCTGATT<br>CTTAAAAAAAAAGGTTTGAAAAAAATGATTTTTTT<br>CAAACTTTTCTTTTCTTTAGAAGTCGAAGTCGTA<br>GAAAATTCTGAAGAATTTAAATTTTAAATTCTTTA<br>GCTTAAAAAAAAAAATTGTCATTCCT |
| 39 | 5' flanking region forward primer | ACATGTATAAAAAAAAGAAAAAGGAAAAAAAAAGA<br>TCAAAAAGGTCTACTTAA |
| 40 | 5' flanking region reverse primer | ACGCGTTTTCAAAACCAACTTCTTGATTGAAACT<br>AAGT |
| 41 | 3' flanking region forward primer | AGCGCTTCCTTGTTACGGTGGATTTTTAGCTATT<br>GC |
| 42 | 3' flanking region reverse primer | GGCGCCAGGAATGACAATTTTTTTTTTAAGCTAA<br>AG |

*E. coli* (Dh5a) was transformed with the vector/construct. Individual colonies were manually picked and tested for the presence of a correct VP28 expression cassette by digestion with XhoI+EcoRI+HindIII. FIG. 12 depicts an annotated photograph of the results from colony #6, which displayed bands at the correct sizes (627bp and 529bp).

Figure 13:
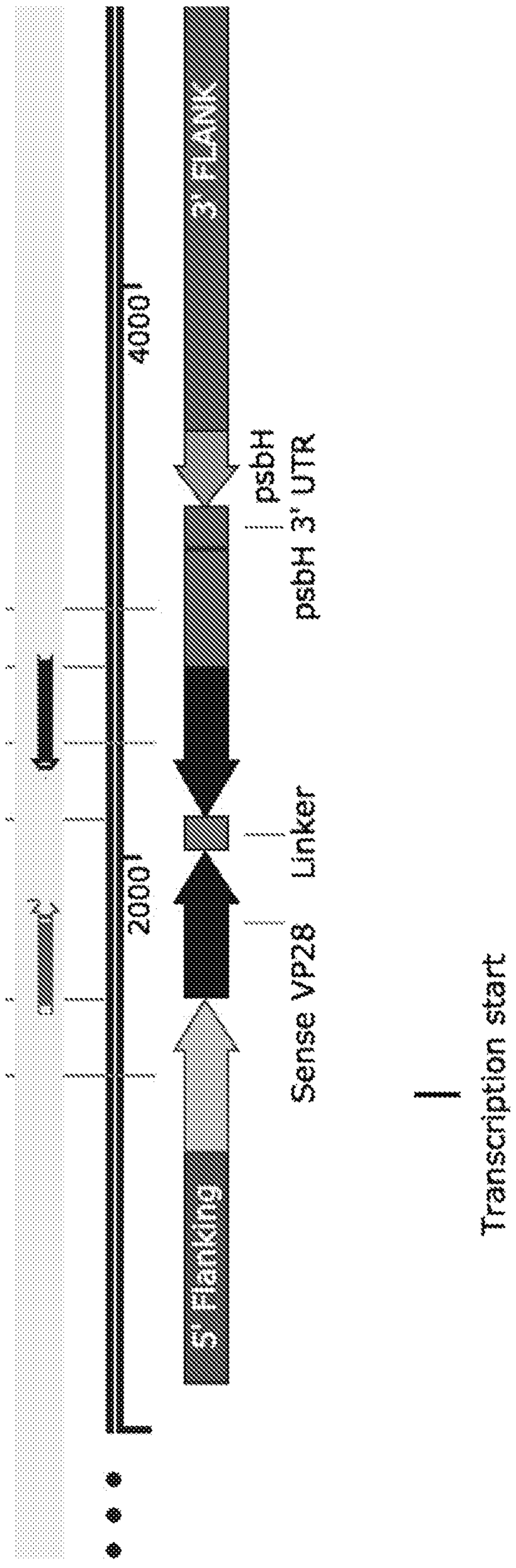
FIG. 13 demonstrates the arrangement of sense and antisense VP28 configured to form dsRNA and flanked by recombination sequences configured for homologous recombination with Chlorella vulgaris.

A shown in FIG. 13, colony #6 was then sequenced confirming the presence of the nucleic acid construct having a heterologous nucleotide sequence embodied as a VP28 sense sequence joined to a VP28 antisense sequence by a linker sequence, and which is operably linked to a constitutively active promoter embodied as a 16S rrn promoter; and a 5' recombination sequence at a 5' end of the construct and a 3' recombination sequence at a 3' end of the construct, that are configured for homologous recombination into a genome of *Chlorella vulgaris*.

Example II

Figure 14:
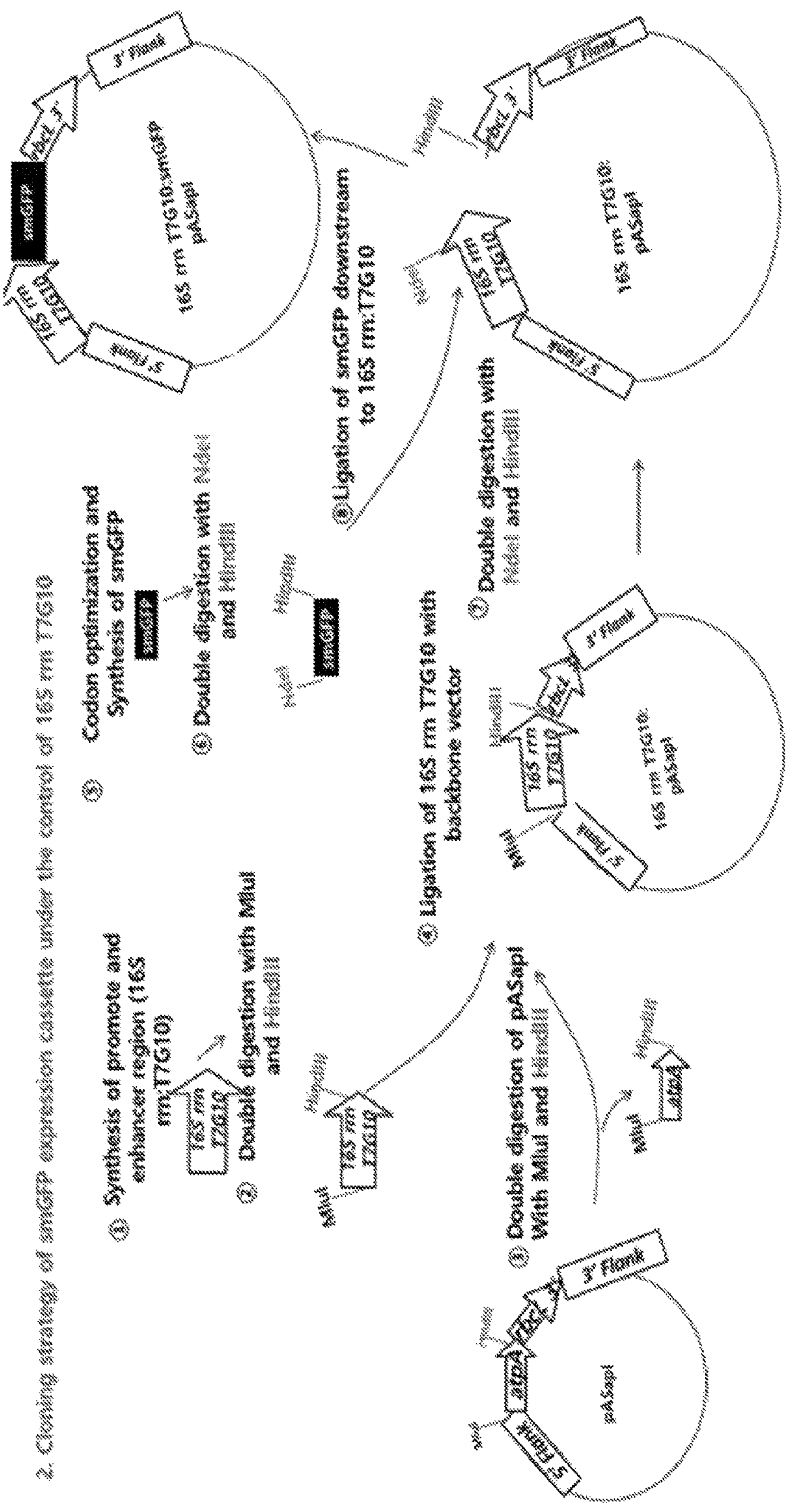
FIG. 14 demonstrates a summary of a cloning strategy followed to generate a vector with expression cassette configured for homologous recombination with *Chorella vulgaris* and expression of green fluorescent protein (GFP).
Figure 15:
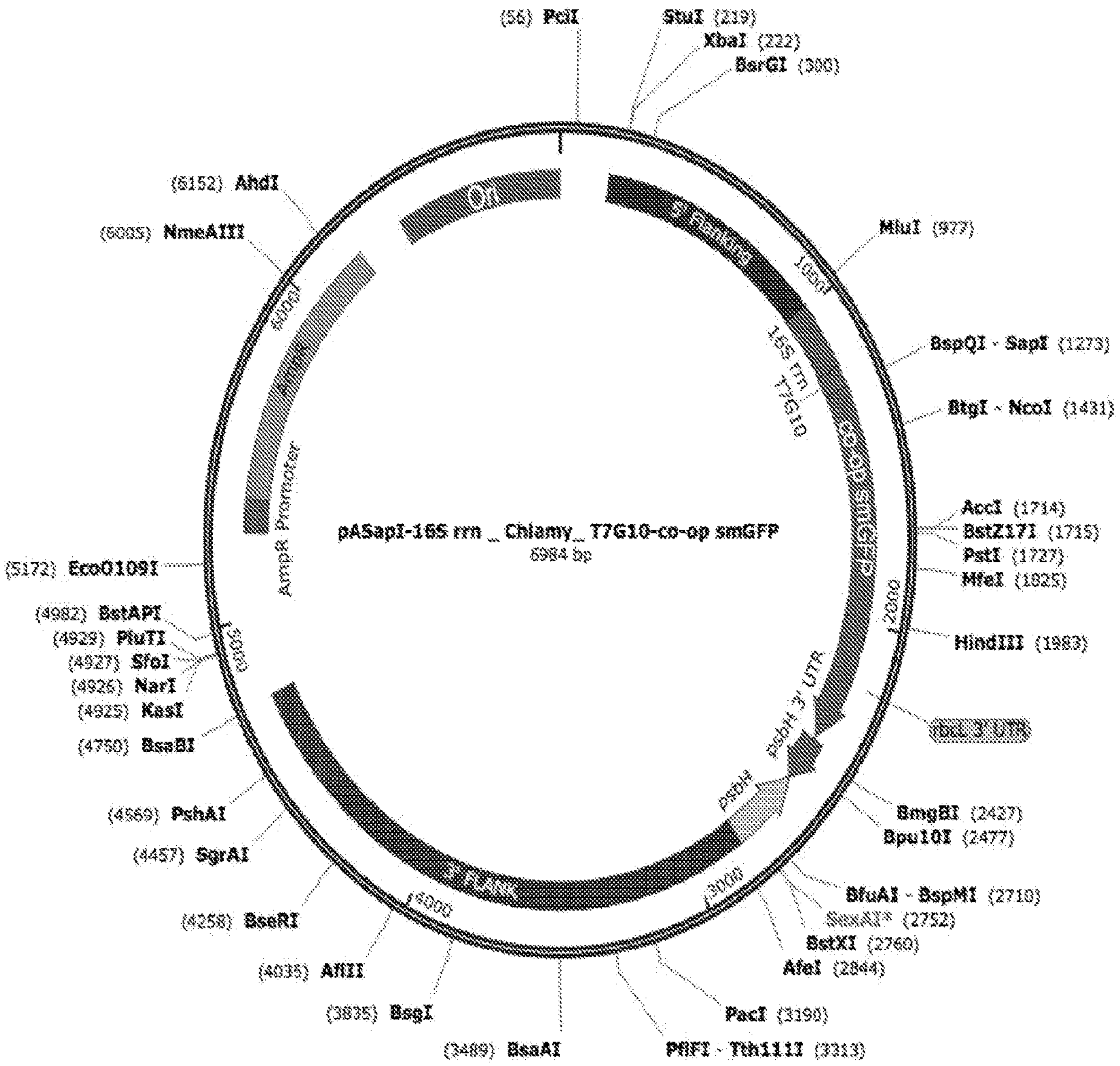
FIG. 15 is a vector map with nucleic acid construct with a heterologous nucleotide sequence, which encodes green fluorescent protein, operably linked to a constitutively active promoter in the form of 16S rrn; 5' and 3' recombination sequences configured for homologous recombination into a genome of a microalgal host cell; and a bacterial 5' untranslated region (5'UTR) and a bacterial 3' untranslated region (3'UTR).

Construction of a Vector with Expression Cassette for Integrating Codon-Optimized GFP Into *Chlorella vulgaris* Chloroplasts The pAsapI vector was once again used as the backbone for the cloning experiment. The sequence for 16S rrn with T7g10 5'UTR (SEQ ID NO: 43) was synthesized using Thermo Fisher Gene Art service. mGFP was also codon optimized based on the codon usage frequencies from rbcL and psbA of *Chlorella vulgaris*, which are two most highly expressed chloroplast genes in *Chlorella vulgaris, Chlorella variabilis* and *Chlorella mirabilis*, and synthesized using Thermo Fisher's Gene Art Service, and was built with NdeI and HindIII cut sites in the 5' and 3' regions, respectively (SEQ ID NO: 44). An overview of the cloning strategy is depicted in FIG. 14 and the final vector is shown in FIG. 15. The promoter and 5'UTR regions were amplified using Forward Primer with a built in cut site for MluI (SEQ ID NO: 45), and Reverse Primer with a built in cut site for HindIII (SEQ ID NO: 46).

TABLE 8

| mGFP & 5'UTR | | |
|---|---|---|
| SEQ ID NO: | Description | Sequence |
| 43 | *Chlorella* 16S rrn (129 bp) + T7G10 (Protein expression) | taaagaaaagtgagctattaacgcgtATCAAAGTTAAATTCGTAA<br>ATTTTAACTTTGATTCTTCTGGAAGTGCAACTACTTTC<br>CGTTTAGCTGGTTGAAATCTTTAGTATAAATTTTTTTT<br>TAAGCAAAAAATTTAATTTAACTATGATAAATTTGGGA<br>GACCACAACGGTTTTCCCaCTAGAAATAATTTTGTTTA<br>ACTTTAAGAAGGAGATATACATATGccctaagcttgtactcaa<br>gctcgtaacg |

TABLE 8-continued

| mGFP & 5'UTR | | |
|---|---|---|
| SEQ ID NO: | Description | Sequence |
| 44 | Codon optimized with restriction sites | TAACTTTAAGAAGGAGATATACATATGTCTAAAGGAG<br>AAGAGCTTTTTACTGGTGTTGTACCAATCTTAGTTGA<br>ATTAGATGGTGATGTTAATGGGCACAAATTCTCTGTA<br>AGTGGTGAAGGTGAAGGTGATGCAACATACGGTAAA<br>TTAACTCTTAAATTTATTTGTACTACTGGTAAATTACC<br>TGTTCCATGGCCAACATTAGTAACTACTTTCTCTTAT<br>GGTGTTCAATGTTTTTCACGTTACCCAGATCATATGA<br>AACGTCACGACTTCTTCAAATCTGCTATGCCTGAAGG<br>TTACGTTCAAGAACGTACTATTTCTTTCAAAGACGAT<br>GGGAACTACAAAACTCGTGCTGAAGTTAAATTTGAAG<br>GTGACACTTTAGTAAACCGTATTGAGTTAAAAGGAAT<br>CGACTTCAAAGAGGATGGTAATATCCTTGGCCACAA<br>ATTAGAATATAACTACAACTCACACAACGTATACATC<br>ACTGCAGACAAACAAAAAAATGGTATCAAAGCTAACT<br>TCAAAATTCGTCACAACATTGAAGATGGTAGCGTTCA<br>ACTAGCAGATCATTACCAACAAAACACTCCAATTGGC<br>GATGGCCCTGTACTTTTACCAGACAACCATTACTTAT<br>CAACTCAATCTGCTTTATCTAAAGATCCTAACGAAAA<br>AAGAGATCACATGGTATTACTTGAATTTGTAACAGCT<br>GCTGGGATTACACATGGCATGGATGAACTATACAAAT<br>AAaagcttgtactcaagctcgtaacgaa |
| 45 | 5'UTR forward primer | taaagaaaagtgagctattaacgcgtggcaggcaacaaatttatttatt<br>gtcccg |
| 46 | 5' UTR reverse primer | cgttacgagcttgagtacaagcttCATATGTATATCTCCTTC<br>TTAAAGTTAAACAAAATTATTTCTAGtGGGAAAAC<br>CGTTGTGGTCTCCCac |

The 16s rrn T7g10 promoter/UTR region, and the pASapI backbone were both digested with MluI and HindIII to remove the atpA promoter in pASapI and to facilitate the joining of the 5' and 3' overhangs of the insert and the construct. The insert was ligated into the pAsapI backbone using T4 DNA ligase. The resultant construct, as well as the mGFP insert, were digested with NdeI and HindIII to facilitate restriction cloning into the DNA backbone. The fragment and the insert were then ligated together using T4 DNA ligase.

Figure 16A:
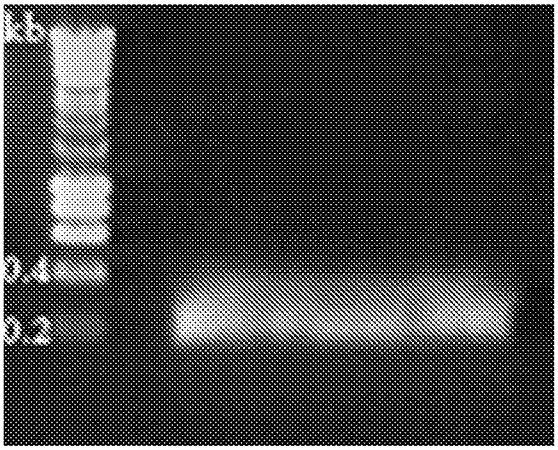
FIG. 16A is an annotated photograph of an agarose gel after PCR amplification of Chlorella 16S rrn: T7G10 promoter confirming insertion of the 5'UTR and promoter in the construct.

Lastly, the 5' and 3' recombination sequences were amplified from the chlorella genome and cloned into the Expression vector. The 5' Recombination site was amplified from chlorella genomic DNA using Forward Primer containing Pcl1 cut site (SEQ ID NO: 39) and Reverse Primer containing the Mlu1 cut site (SEQ ID NO: 40). Results are shown in FIG. 16A.

The resulting PCR product and the pASapI backbone were then digested with Mlu1 and pcl1, and the overhangs of the insert and the template were joined together using T4 DNA ligase. A similar procedure was employed for the 3' Recombination site, using Forward Primer containing Afe1 restriction site (SEQ ID NO: 41) and a Reverse Primer with restriction site KasI (SEQ ID NO: 42) to amplify the desired region from chlorella vulgaris genomic DNA. The fragment and the insert (pASapI) were both digested with Afe1 and KasI, and the complementary overhangs were joined together using T4 DNA ligase.

Figure 16B:
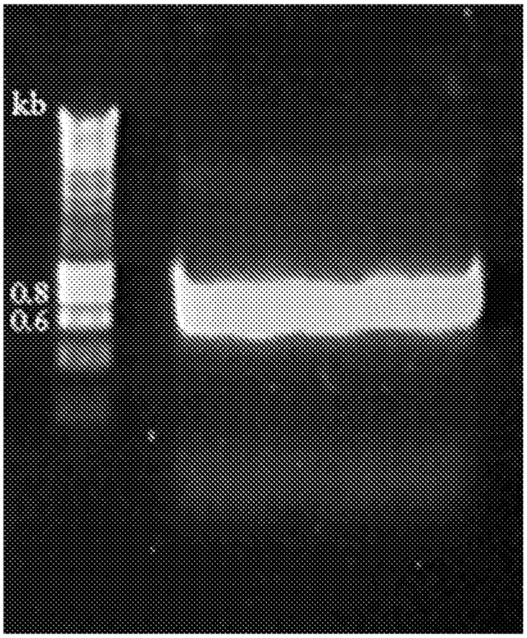
FIG. 16B is an annotated photograph of an agaorse gel after PCR amplification of co-op smGFP confirming insertion in the construct.

*E. coli* (Dh5a) was transformed with the vector/construct. Individual colonies were manually picked and tested for the presence of a correct GFP expression cassette by digestion. Results are shown in FIG. 16B.

REFERENCES

1. Dreesen, I. A. J., Charpin-El Hamri, G. and Fussenegger, M. (2010) Heat-stable oral alga-based vaccine protects mice from *Staphylococcus aureus* infection. *J. Biotechnol.,* 145, 273-280.

2. Richards, J. E. and Scott Hawley, R. (2011) The Central Dogma of Molecular Biology. In *The Human Genome*. pp. 83-113.

3. van Hulten, M. C. W., Reijns, M., Vermeesch, A. M. G., Zandbergen, F. and Vlak, J. M. (2002) Identification of VP19 and VP15 of white spot syndrome virus (WSSV) and glycosylation status of the WSSV major structural proteins. *J. Gen. Virol.,* 83, 257-265.

4. Thammasorn, T., Sangsuriya, P., Meemetta, W., Senapin, S., Jitrakorn, S., Rattanarojpong, T. and Saksmerprome, V. (2015) Large-scale production and antiviral efficacy of multi-target double-stranded RNA for the prevention of white spot syndrome virus (WSSV) in shrimp. *BMC Biotechnol.,* 15, 110.

5. Economou, C., Wannathong, T., Szaub, J. and Purton, S. (2014) A simple, low-cost method for chloroplast transformation of the green alga *Chlamydomonas reinhardtii. Methods Mol. Biol.,* 1132, 401-411.

6. Ku, C., Nelson-Sathi, S., Roettger, M., Sousa, F. L., Lockhart, P. J., Bryant, D., Hazkani-Covo, E., McInerney, J. O., Landan, G. and Martin, W. F. (2015) Endosymbiotic origin and differential loss of eukaryotic genes. *Nature,* 524, 427-432.

7. Driks, A. (1999) Spatial and Temporal Control of Gene Expression in Prokaryotes. In *Development. pp.* 21-33.

8. Yang, H., Gray, B. N., Ahner, B. A. and Hanson, M. R. (2013) Bacteriophage 5' untranslated regions for control of plastid transgene expression. *Planta,* 237, 517-527.

9. Tsunoyama, Y., Ishizaki, Y., Morikawa, K., Kobori, M., Nakahira, Y., Takeba, G., Toyoshima, Y. and Shiina, T. (2004) Blue light-induced transcription of plastid-encoded psbD gene is mediated by a nuclear-encoded transcription initiation factor, AtSig5. *Proc. Natl. Acad. Sci. U.S.A.,* 101, 3304-3309.

10. Kung, S. D. and Lin, C. M. (1985) Chloroplast promoters from higher plants. *Nucleic Acids Res.,* 13, 7543-7549.

What is claimed is:

1. A nucleic acid construct for producing double stranded RNA (dsRNA), the nucleic acid construct comprising:

a) a heterologous nucleotide sequence operably linked to a 5' untranslated region (5'UTR), a constitutively active promoter selected from the group consisting of a 16s rrn promoter, an atpB promoter, an atpF promoter, a tufA promoter, a rbcL promoter, and a psaA promoter, and a 3' untranslated region (3'UTR), wherein transcription of the heterologous nucleotide sequence produces interfering double stranded RNA (dsRNAi); and b) a 5' recombination sequence at a 5' end of the construct and a 3' recombination sequence at a 3' end of the construct, wherein the recombination sequences are configured for homologous recombination into a genome of a microalgal host cell, further wherein the 5'UTR is between the 5' recombination sequence and the promoter, and the 3'UTR is between the heterologous nucleotide sequence and the 3' recombination sequence;

further wherein:

the 5'UTR is selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26; and the 3'UTR is selected from the group consisting of a rbcL 3'UTR, a 16s rrn 3'UTR, an atpA 3'UTR, and a psA 3'UTR.

2. The nucleic acid construct according to claim 1, wherein the heterologous nucleotide sequence comprises a sense sequence joined to an antisense sequence by a linker sequence configured to form a loop structure after transcription.

3. The nucleic acid construct according to claim 1, wherein the dsRNA is configured to silence VP28 translation.

4. A nucleic acid construct comprising:

a) a multicloning site configured for cleavage by a plurality of different restriction endonucleases;

b) a constitutively active promoter that directs transcription towards the multicloning site, wherein the promoter is selected from the group consisting of a 16s rrn promoter, an atpB promoter, an atpF promoter, a tufA promoter, a rbcL promoter, and a psaA promoter;

c) a 5' recombination sequence at a 5' end of the construct and a 3' recombination sequence at a 3' end of the construct, wherein the recombination sequences are configured for homologous recombination into a genome of a microalgal host cell; and d) a 5' untranslated region (5'UTR) between the 5' recombination sequence and the promoter, and a bacterial 3' untranslated region (3'UTR) between the 3' recombination sequence and the multicloning site, wherein:

the 5'UTR is selected from the group consisting of SEQ ID NO: 19, SEQ ID NO: 20, SEQ ID NO: 21, SEQ ID NO: 22, SEQ ID NO: 23, SEQ ID NO: 24, SEQ ID NO: 25, and SEQ ID NO: 26; and the 3'UTR is selected from the group consisting of a rbcL 3'UTR, a 16s rrn 3'UTR, an atpA 3'UTR, and a psA 3'UTR.

5. A vector comprising a nucleic acid sequence comprising the nucleic acid construct according to claim 1.

6. A host cell transformed with the nucleic acid construct according to claim 5.

7. A biomass comprising the host cell according to claim 6 in a dried form.

8. The nucleic acid construct according to claim 1, wherein: when the 3' UTR is the rbcL 3'UTR, the 3'UTR is SEQ ID NO: 28, when the 3' UTR is the 16s rrn 3'UTR, the 3'UTR is SEQ ID NO: 29, when the 3' UTR is the atpA 3'UTR, the 3'UTR is SEQ ID NO: 30, and when the 3' UTR is the psaA 3'UTR, the 3'UTR is SEQ ID NO: 31.

9. The nucleic acid construct according to claim 1, wherein the 5'UTR is SEQ ID NO: 19 and the promoter is the 16s rrn promoter.

10. The nucleic acid construct according to claim 4, wherein the 5'UTR is SEQ ID NO: 19 and the promoter is the 16s rrn promoter.

* * * * *

SEQUENCE LISTING

<160> NUMBER OF SEQ ID NOS: 46

<210> SEQ ID NO 1
<211> LENGTH: 1163
<212> TYPE: DNA
<213> ORGANISM: artificial sequence
<220> FEATURE:
<223> OTHER INFORMATION: synthetic construct

<400> SEQUENCE: 1
tctagaatgg atctttcttt cactctttcg gtcgtgtcgg ccatcctcgc catcactgct 60
gtgattgctg tatttattgt gatttttagg tatcacaaca ctgtgaccaa gaccatcgaa 120
acccacacag acaatatcga gacaaacatg gatgaaaacc tccgcattcc tgtgactgct 180
gaggttggat caggctactt caagatgact gatgtgtcct ttgacagcga caccttgggc 240
aaaatcaaga tccgcaatgg aaagtctgat gcacagatga aggaagaaga tgcggatctt 300
gtcatcactc ccgtggaggg ccgagcactc gaagtgactg tggggcagaa tctcaccttt 360
gagggaacat tcaaggtgtg gaacaacaca tcaagaaaga tcaacatcac tggtatgcag 420
atggtgccaa agattaaccc atcaaaggcc tttgtcggta gctccaacac ctcctccttc 480
acccccgtct ctattgatga ggatgaagtt ggcacctttg tgtgtggtac cacctttggc 540
gcaccaattg cagctaccgc cggtggaaat cttttcgaca tgtacgtgca cgtcacctac 600
tctggcactg agaccgagta aaagggcgaa ttcgccctta cacaaaggtg ccaacttcat 660
cctcatcaat agagacgggg gtgaaggagg aggtgttgga gctaccgaca aaggcctttg 720
atgggttaat ctttggcacc atctgcatac cagtgatgtt gatctttctt gatgtgttgt 780
tccacacctt gaatgttccc tcaaaggtga gattctgccc cacagtcact tcgagtgctc 840
ggccctccac gggagtgatg acaagatccg catcttcttc cttcatctgt gcatcagact 900
ttccattgcg gatcttgatt ttgcccaagg tgtcgctgtc aaaggacaca tcagtcatct 960
tgaagtagcc tgatccaacc tcagcagtca caggaatgcg gaggttttca tccatgtttg 1020
tctcgatatt gtctgtgtgg gtttcgatgg tcttggtcac agtgttgtga tacctaaaaa 1080
tcacaataaa tacagcaatc acagcagtga tggcgaggat ggccgacacg accgaaagag 1140
tgaaagaaag atccatgctg agc 1163

<210> SEQ ID NO 2
<211> LENGTH: 503
<212> TYPE: DNA
<213> ORGANISM: artificial sequence
<220> FEATURE:
<223> OTHER INFORMATION: synthetic construct

<400> SEQUENCE: 2
aaaagaaaaa aataaagaaa gattttaaag cagtttttga ttctagatct agaaaaaaca 60
atattttctt ttagaacata aacggtctaa aatttagttt aaactgtagg catcctattt 120
acaaattaca tagttttttt tagtaaaaaa aatgtatttt ttccaaaagt taaaagtttg 180
aaaaaataaa tttaaacaca aagaccagaa caaaaaaaaa cttttctcaa caaaaaatag 240
aattaaaatc aaagttaaat tcgtaaattt taactttgat tcttctggaa gtgcaactac 300
tttccgttta gctggttgaa atctttagta taaatttttt tttaagcaaa aaatttaatt 360

-continued

```
taactatgat aaatttaaaa attaaagcaa ggaaaaaaag aagagagagg aagactggtt    420

tgactttttt tttattaaag atacattact aagtgtgaaa acaaaaaatt ttcatggaga    480

gtttgatcct ggctcaggat gaa                                            503


<210> SEQ ID NO 3
<211> LENGTH: 69
<212> TYPE: DNA
<213> ORGANISM: n. tabacum

<400> SEQUENCE: 3

aagtaaaaaa gaaaaattgg gttgcctata tatatgaaga gtatacaata atgatgtatt     60

tggcaaatc                                                             69


<210> SEQ ID NO 4
<211> LENGTH: 71
<212> TYPE: DNA
<213> ORGANISM: N. otophora

<400> SEQUENCE: 4

aagtaaaaaa gaaaaattgg gttgcgctat atatatgaaa gagtatacaa taatgatcta     60

tttggcaaat c                                                          71


<210> SEQ ID NO 5
<211> LENGTH: 70
<212> TYPE: DNA
<213> ORGANISM: N. tabacum

<400> SEQUENCE: 5

tcaggttcga attccataga atagataata tggatgggat tgtctataat gatagacaaa     60

tgaaagactt                                                            70


<210> SEQ ID NO 6
<211> LENGTH: 70
<212> TYPE: DNA
<213> ORGANISM: N. otophora

<400> SEQUENCE: 6

tcaggttcga attccataga atagataata tggatgggat tgtctataat gatagacaaa     60

tgaaagactt                                                            70


<210> SEQ ID NO 7
<211> LENGTH: 72
<212> TYPE: DNA
<213> ORGANISM: N. tabacum

<400> SEQUENCE: 7

ggtgtcccct ccagtcaaga attggggcct cacaatcact agccaatatg cttttctctc     60

atgcctttct tc                                                         72


<210> SEQ ID NO 8
<211> LENGTH: 70
<212> TYPE: DNA
<213> ORGANISM: N. tabacum

<400> SEQUENCE: 8

agttgttcaa gaatagtccc gttgagtttc tcgacccttt gacttaggat tagtcagttc     60

tatttctcga                                                            70
```

<210> SEQ ID NO 9
<211> LENGTH: 60
<212> TYPE: DNA
<213> ORGANISM: N. tabacum

<400> SEQUENCE: 9
tgattaccac aattcccctg ttcgacaaaa gttgcatttg tatacaataa tcggattgta 60

<210> SEQ ID NO 10
<211> LENGTH: 69
<212> TYPE: DNA
<213> ORGANISM: maize

<400> SEQUENCE: 10
aataaagatt agggtttggg ttgcgctata tctatcaaga gtatacaata atgatggatt 60
tggtgaatc 69

<210> SEQ ID NO 11
<211> LENGTH: 69
<212> TYPE: DNA
<213> ORGANISM: maize

<400> SEQUENCE: 11
aatactaaga aaattctctg ttgacagcaa tctatccttc acagtagtat atattttgta 60
tatcgggtc 69

<210> SEQ ID NO 12
<211> LENGTH: 71
<212> TYPE: DNA
<213> ORGANISM: Maize

<400> SEQUENCE: 12
atggatagga ggcttgtggg attgacgtga tagggtaggg ttgcctatac tgctggtggc 60
gaactccagg c 71

<210> SEQ ID NO 13
<211> LENGTH: 74
<212> TYPE: DNA
<213> ORGANISM: Maize

<400> SEQUENCE: 13
tcctattttc cataggaccg gttgacaatt gaatccaatt tttcccatta tttgactgtc 60
cataatagtg ccga 74

<210> SEQ ID NO 14
<211> LENGTH: 67
<212> TYPE: DNA
<213> ORGANISM: Maize

<400> SEQUENCE: 14
aagcccgaaa gagtggcctt gcgtttctcg cccctttgcc ttaggattcg ttaattctct 60
ttctcga 67

<210> SEQ ID NO 15
<211> LENGTH: 65
<212> TYPE: DNA
<213> ORGANISM: Maize

<400> SEQUENCE: 15
tcagaataaa tagaataata atgaatgaaa aagagaaaat ccttgaatga aaaagagaaa 60

-continued atcct 65

<210> SEQ ID NO 16
<211> LENGTH: 71
<212> TYPE: DNA
<213> ORGANISM: Spinach

<400> SEQUENCE: 16
aaaccaacgg ttacggttgg gttgcgccat atatatgaaa gagtatacaa taatgatgta 60
tttgccgaat c 71

<210> SEQ ID NO 17
<211> LENGTH: 68
<212> TYPE: DNA
<213> ORGANISM: Spinach

<400> SEQUENCE: 17
aatactaata aattctttgt tgacagtggt atatgttgta tatgtatatc ctagatgtga 60
aaatatgc 68

<210> SEQ ID NO 18
<211> LENGTH: 48
<212> TYPE: DNA
<213> ORGANISM: C. reihnhardtii

<400> SEQUENCE: 18
aagtaatggt tcacccttgt catatttaaa tactaaaatt catttgcc 48

<210> SEQ ID NO 19
<211> LENGTH: 64
<212> TYPE: DNA
<213> ORGANISM: T7 bacteriophage

<400> SEQUENCE: 19
gggagaccac aacggttttc ccactagaaa taattttgtt taactttaag aaggagatat 60
acat 64

<210> SEQ ID NO 20
<211> LENGTH: 252
<212> TYPE: DNA
<213> ORGANISM: C. vulgaris

<400> SEQUENCE: 20
gatgaaaaaa agatcaaaaa gaaaaaaaag ctagagaaaa tcaaggtttg aaaaaaaata 60 tttttttca tgccttgatt ttctttagaa agagaaaaat aatgaatttt tcaacagtag 120
aacagaatca aaagaatttc actcttgtga tactctaaaa aatatgctat actctggtgt 180
aaaacaaaaa gacaagaaat tacacttttt ttcgggcaga gtgcaagatc gtaaaccata 240 attttttta ga 252

<210> SEQ ID NO 21
<211> LENGTH: 250
<212> TYPE: DNA
<213> ORGANISM: C. vulgaris

<400> SEQUENCE: 21
aaaaattaaa atgtttttc tttttccta aaaaggagtt tttcccaaaa ttaaaaaaat 60
ttaatttgtt aggccctact gtaactaaaa tctaaatctc agtcaagtaa ctattaaaat 120
aaagattaaa ataaacaaaa aggctactcg atttaaaatt aggtttttat attaatttga 180
aaaacttttt ttaacaagta aaaaaagaag aaaaaatact ctaattctta agattttcaa 240
cacataaatt 250

<210> SEQ ID NO 22
<211> LENGTH: 285
<212> TYPE: DNA
<213> ORGANISM: c. vulgaris

<400> SEQUENCE: 22
ggtacttctg aactgcctcc tctttgttac aaaactcgac gttttgccat tcatattgta 60
ttaactggct ttagaattcg taaaaagcac aatttgaaaa ttattcactg cactatgaat 120
tgaagaagtt aatcgttgat taagtttttc gcgaacttgt tgtaatgcca gttttactaa 180
tttttccgca agttcatttt gagctttttg ttgctcaaac tttaaggtct cctgttggag 240
agtacctaaa cgttttatat cttcttgtgt ttggcgaatg aattg 285

<210> SEQ ID NO 23
<211> LENGTH: 313
<212> TYPE: DNA
<213> ORGANISM: C. vulgaris

<400> SEQUENCE: 23
gaaaaaaaaa cggaatcaga aaagaaagaa atgacaaaaa aatgattttt ttcattccat 60
ttttttttta gaaaaaaaaa cgaaaattaa ggcatttatt tttttaagga tcaaaaagat 120 tttttttca agcctatctt tttttttcta aaaaaaaaga agggtggaac ccttcatttt 180
ctgattccat tttttttttt taagaaagaa aatcttgatt ttagaacttt tttagctctt 240
ttttaaattg ggcttttgtt tgatattctt ttgtacaaat taaagaaaac actaaaacct 300
ttccacccta agt 313

<210> SEQ ID NO 24
<211> LENGTH: 400
<212> TYPE: DNA
<213> ORGANISM: C. vulgaris

<400> SEQUENCE: 24
gtttcattta aacgaaaatt gtactgagtg ttttaaccaa aatttaagca cctttgcaga 60
tttcgtcatc tttcttttt ttgaaaaaaa aagaaataaa aagaaaaaaa gctgttttaa 120
actgaatagt aactaaccct ttatgcacca gagttctatg ggatcctata acgaaactct 180
caagttactc ttttgtgagt acaatcaaac gcaagactca tatttctgtc tagtgatttt 240
gtaaattttt ggaactacca aaaattagaa cttttggttt caaatttcaa ctttgtcatt 300 atttttttg attttcttaa ccgctatttt ttttaaaaat actgtggtaa gattttaaaa 360
aagataattt cggtaattca aataaggaga atttttcgcc 400

<210> SEQ ID NO 25
<211> LENGTH: 80
<212> TYPE: DNA
<213> ORGANISM: T7 bacteriophage

<400> SEQUENCE: 25
tacgactcag tatagggaca atgcttaagg tcgctctcta ggagtggcct tagtcattta 60
accaatagga gataaacatt 80

<210> SEQ ID NO 26

-continued

<211> LENGTH: 240
<212> TYPE: DNA
<213> ORGANISM: C. vulgaris

<400> SEQUENCE: 26
aatttcaagg gtagtagaat ttttttact ttctgtaacg agaaaactaa aagaaagttt 60
tataaatttt aaatcatttt agttttcgat tttaacgtca attttttcag actttcttcc 120
aattttatta tatagtaaat tttaaattgg aaaaaggttt tagttacttc tttcgaaaac 180
gcaactaaaa gtataaaatg ttttttgaaa acaaaatttt tagtttcttt aaagttttta 240

<210> SEQ ID NO 27
<211> LENGTH: 367
<212> TYPE: DNA
<213> ORGANISM: c.vulgaris

<400> SEQUENCE: 27
ccttttaaag gataaaaaaa ccttaagaaa aaacaaagtt tttcttaagt actccaatcc 60
ttctttcttt ttttattccc attaaattga ataaaaatta aacgttttct tactttaatg 120
agaatataaa ttaagatgat ttccgttttt tgaaatccag tttttggttt tttttttcct 180
tctttttttt ttataaaaaa aaagatcaaa atgaatcaaa aactaataga aaaaaacgga 240
atttgaagaa ttgattcatt ttttacatgt gcatgagtca ctagcttgct tttttagtgc 300
actaacctct tctccaaaaa tttttcaaac caaaatttat gggaagaaga gagtgggaaa 360
aaacaac 367

<210> SEQ ID NO 28
<211> LENGTH: 169
<212> TYPE: DNA
<213> ORGANISM: C. vulgaris

<400> SEQUENCE: 28
ttttcaacta aactgttcca gttctaaaga aaattaagga aaatccttaa ttttctttaa 60 cttttttttct ttttttttct tctttttgat cttttttttt ttataaaaaa aagaaaaagg 120
aaaaaaaaga tcaaaaaggt ctacttaaaa acataaatgc cttgcattt 169

<210> SEQ ID NO 29
<211> LENGTH: 316
<212> TYPE: DNA
<213> ORGANISM: C.vulgaris

<400> SEQUENCE: 29
ccttttaaag gataaaaaaa ccttaagaaa aaacaaagtt tttcttaagt actccaatcc 60
ttctttcttt ttttattccc attaaattga ataaaaatta aacgttttct tactttaatg 120
agaatataaa ttaagatgat ttccgttttt tgaaatccag tttttggttt tttttttcct 180
tctttttttt ttataaaaaa aaagatcaaa atgaatcaaa aactaataga aaaaaacgga 240
atttgaagaa ttgattcatt ttttacatgt gcatgagtca ctagcttgct tttttagtgc 300
actaacctct tctcca 316

<210> SEQ ID NO 30
<211> LENGTH: 254
<212> TYPE: DNA
<213> ORGANISM: C.vulgaris

<400> SEQUENCE: 30
aaaagtatgt tttattagta aagtatcaga tttatacaga gcttaataaa aacagggccc 60
aataaatgaa tgggaaaaat tttaaattat gtttttttta cttttgatct tttttttag 120 ttcttttttt tcttttttttt tttttgaaaa aaaaaagaaa aaaaagaact aaaaaaaaag 180
atcaaaagta aaaaaaacat aaccaaaaaa taccagcaaa gcatgtattt ttttaagggt 240
tgagatactt agtt 254

<210> SEQ ID NO 31
<211> LENGTH: 304
<212> TYPE: DNA
<213> ORGANISM: C.vulgaris

<400> SEQUENCE: 31
gaaaaccagg caaaaaattt cgtttctctt actttaaaga attggaaagg tttctgattc 60
cacaaaaaaa atgcgaagca ttttttata attccttttt ttgctcttcc taaaaaaaaa 120
atgcaaagca ttttttttta ggataatttc tgattctttt tgatcttttt tttttagttc 180
tttttgatgt ttttttttt ataaaaaaaa aacaaataga aaaaaaagaa aaaaaagaag 240
caaaaaaaga tcaaaaagga aatagtaggc aggtttccaa cttaaaaaat taaaagcaaa 300
gctt 304

<210> SEQ ID NO 32
<211> LENGTH: 40
<212> TYPE: DNA
<213> ORGANISM: artificial sequence
<220> FEATURE:
<223> OTHER INFORMATION: synthetic construct

<400> SEQUENCE: 32
taaaattctc gagatggatc tttctttcac tctttcggtc 40

<210> SEQ ID NO 33
<211> LENGTH: 26
<212> TYPE: DNA
<213> ORGANISM: artificial sequence
<220> FEATURE:
<223> OTHER INFORMATION: synthetic construct

<400> SEQUENCE: 33
ccgagtaaaa gggcgaattc gccctt 26

<210> SEQ ID NO 34
<211> LENGTH: 26
<212> TYPE: DNA
<213> ORGANISM: artificial sequence
<220> FEATURE:
<223> OTHER INFORMATION: synthetic construct

<400> SEQUENCE: 34
ccgagtaaaa gggcgaattc gccctt 26

<210> SEQ ID NO 35
<211> LENGTH: 37
<212> TYPE: DNA
<213> ORGANISM: artificial sequence
<220> FEATURE:
<223> OTHER INFORMATION: synthetic construct

<400> SEQUENCE: 35
gagtacaagc ttatggatct ttctttcact ctttcgg 37

<210> SEQ ID NO 36

-continued

<211> LENGTH: 266
<212> TYPE: DNA
<213> ORGANISM: artificial sequence
<220> FEATURE:
<223> OTHER INFORMATION: synthetic construct

<400> SEQUENCE: 36
taaagaaaag tgagctatta acgcgtatca aagttaaatt cgtaaatttt aactttgatt 60
cttctggaag tgcaactact ttccgtttag ctggttgaaa tctttagtat aaattttttt 120
ttaagcaaaa aatttaattt aactatgata aatttaaaaa ttaaagcaag gaaaaaaaga 180
agagagagga agactggttt gacttttttt ttattaaaga tacattacta agtgtgaaaa 240
caaagcttgt actcaagctc gtaacg 266

<210> SEQ ID NO 37
<211> LENGTH: 1100
<212> TYPE: DNA
<213> ORGANISM: C. vulgaris

<400> SEQUENCE: 37
ataaaaaaaa gaaaaaggaa aaaaaagatc aaaaaggtct acttaaaaac ataaatgcct 60
tgcatttatg tttttaagga taaaaaatat ttttggccgt ctttcttttc ttaagctttt 120
ttttcaaaag cttaagaaaa gaaaagattt tcctttattt tttttagaac cggaacaaac 180
ttttgaaaaa aaatttactt ttttttcatc agtcctccat tgaaaatgga gagtcccctt 240
cttttttttt ataaaaaaaa gaatgaaaag aaatgctttg tatttctttt ctttaggaaa 300
aaataaaatt ttttcatttt aactgatact aaaattcgtt tctttttttt gtgtaataaa 360
ataaaaaaga aataaataac tgaacctaga tatggcaaaa aaaagcatga ttgagcgtga 420
tagaaaacgc gctcgtttaa ttactaaata tgcagcaaaa cgaaaaaatc tcctcgtaga 480
aattaaaaca gcaacttctt tagaagacaa attcaattta catagaaaat tgcaacaact 540
accaagaaat agtgcaccag ttcgatctca taatcgttgt acaattaccg gtcggcccag 600
aggatatttt agagacttcg gcttatcccg ccatgtttta cgcgaatatg ctttacaagg 660 tttttttacct ggtgtggtaa aagctagttg gtaaaaaaac tgtagttgac ctattgactt 720
ttgatttccg ttcttgtctt ttctttttga gctttttttt ataaaaaaaa aagaaaaaaa 780
agctcaaaaa gaaaaactac acattattaa agcgtcgcga tctgggtatc agaaacaaaa 840
gcgacatggt gattacataa ttttaaagga aagctacatg gtgattacat gattttaaag 900
gaaaattaca tagtgattac ataacgtttt tagcgaataa accttgccaa tacagcattt 960
ttttcttttt tttttttttt aatgtgatat ttaagtcgtt taatttttca acacgttttt 1020
tttaacaact ttcgaaataa caactttaac caacttgttt ttagccttac ttagtttcaa 1080
tcaagaagtt ggttttgaaa 1100

<210> SEQ ID NO 38
<211> LENGTH: 1120
<212> TYPE: DNA
<213> ORGANISM: C.vulgaris

<400> SEQUENCE: 38
tccttgttac ggtggatttt tagctattgc gctttttcct ttttttagt ataattttta 60 ttacctttta acaagcctgc ttagctcagt tggttagagc atccgtctca tacgcggaat 120
gtcactagtt cgaatctagt agcaggcacc ataatttcgc gggtatagct cagtggtaga 180
gcggcacctt gccaaggtgc atgtcgcgcg ttcgactcgc gttacccgct tattttattt 240

```
tttctattta agttttttca taaaatctaa aattaaaaag agtctattta atccagtttt    300

ttggttcgaa tagtttttcg tttctttttt tcaaaaaaaa aaaagaatga aaaactcaaa    360

aaacaaaaac gggttccacc cttaaaaaaa atgctgtgca tttttttaag taaacccaat    420

gctttttttt tataaaaaaa aagaatgaaa agaaattctt ttttttcat gcctttattt    480

tctttagaac cgaaaatcaa agaaaatttt cttttataaa ttaaatcgtt tctatctttt    540

tttttctaaa aaaaaaagaa ggaaaaaaaa tactttttc aaagttatta cggaatatgt    600

taaatcgagg gtgacgggac tcgaacccgc aacttccacc gtgacagggt ggtgctctga    660

ccaattgaac tacacccccct cgatatggat ttatcatatc acacatcttt tttttaatgt    720

agagctagct gtcagttcca gtacaaattg tctattttat ttattttcaa aaggagataa    780

atctgtcttt taataagttt atagctgaat aaaaaaattt tctcttacga aaataaatgc    840

aaagcactta tttcctgatt tcgtttttta aattgaatag tttttttct tttttcaaa    900

aaaagaaaga aaaactccag gttaaaaaac ggctttgaag cgacttccgt ttttttattc    960

aatgagtttt tctttagaaa aacttctgat tcttaaaaaa aaaggtttga aaaaaatgat   1020

tttttcaaa cttttctttt ctttagaagt cgaagtcgta gaaaattctg aagaatttaa   1080

attttaaatt ctttagctta aaaaaaaaat tgtcattcct                        1120
```

```
<210> SEQ ID NO 39
<211> LENGTH: 52
<212> TYPE: DNA
<213> ORGANISM: artificial sequence
<220> FEATURE:
<223> OTHER INFORMATION: synthetic construct

<400> SEQUENCE: 39

acatgtataa aaaaaagaaa aaggaaaaaa aagatcaaaa aggtctactt aa            52


<210> SEQ ID NO 40
<211> LENGTH: 38
<212> TYPE: DNA
<213> ORGANISM: artificial sequence
<220> FEATURE:
<223> OTHER INFORMATION: synthetic construct

<400> SEQUENCE: 40

acgcgttttc aaaaccaact tcttgattga aactaagt                            38


<210> SEQ ID NO 41
<211> LENGTH: 36
<212> TYPE: DNA
<213> ORGANISM: artificial sequence
<220> FEATURE:
<223> OTHER INFORMATION: synthetic construct

<400> SEQUENCE: 41

agcgcttcct tgttacggtg gatttttagc tattgc                              36


<210> SEQ ID NO 42
<211> LENGTH: 36
<212> TYPE: DNA
<213> ORGANISM: artificial sequence
<220> FEATURE:
<223> OTHER INFORMATION: synthetic construct

<400> SEQUENCE: 42

ggcgccagga atgacaattt ttttttaag ctaaag                               36
```

<210> SEQ ID NO 43
<211> LENGTH: 250
<212> TYPE: DNA
<213> ORGANISM: artificial sequence
<220> FEATURE:
<223> OTHER INFORMATION: synthetic construct

<400> SEQUENCE: 43
taaagaaaag tgagctatta acgcgtatca aagttaaatt cgtaaatttt aactttgatt 60
cttctggaag tgcaactact ttccgtttag ctggttgaaa tctttagtat aaattttttt 120
ttaagcaaaa aatttaattt aactatgata aatttgggag accacaacgg ttttcccact 180
agaaataatt ttgtttaact ttaagaagga gatatacata tgccctaagc ttgtactcaa 240
gctcgtaacg 250

<210> SEQ ID NO 44
<211> LENGTH: 767
<212> TYPE: DNA
<213> ORGANISM: artificial sequence
<220> FEATURE:
<223> OTHER INFORMATION: synthetic construct

<400> SEQUENCE: 44
taactttaag aaggagatat acatatgtct aaaggagaag agctttttac tggtgttgta 60
ccaatcttag ttgaattaga tggtgatgtt aatgggcaca aattctctgt aagtggtgaa 120
ggtgaaggtg atgcaacata cggtaaatta actcttaaat ttatttgtac tactggtaaa 180
ttacctgttc catggccaac attagtaact actttctctt atggtgttca atgtttttca 240
cgttacccag atcatatgaa acgtcacgac ttcttcaaat ctgctatgcc tgaaggttac 300
gttcaagaac gtactatttc tttcaaagac gatgggaact acaaaactcg tgctgaagtt 360
aaatttgaag gtgacacttt agtaaaccgt attgagttaa aaggaatcga cttcaaagag 420
gatggtaata tccttggcca caaattagaa tataactaca actcacacaa cgtatacatc 480
actgcagaca aacaaaaaaa tggtatcaaa gctaacttca aaattcgtca caacattgaa 540
gatggtagcg ttcaactagc agatcattac caacaaaaca ctccaattgg cgatggccct 600
gtacttttac cagacaacca ttacttatca actcaatctg ctttatctaa agatcctaac 660
gaaaaaagag atcacatggt attacttgaa tttgtaacag ctgctgggat tacacatggc 720
atggatgaac tatacaaata aaagcttgta ctcaagctcg taacgaa 767

<210> SEQ ID NO 45
<211> LENGTH: 55
<212> TYPE: DNA
<213> ORGANISM: artificial sequence
<220> FEATURE:
<223> OTHER INFORMATION: synthetic construct

<400> SEQUENCE: 45
taaagaaaag tgagctatta acgcgtggca ggcaacaaat ttatttattg tcccg 55

<210> SEQ ID NO 46
<211> LENGTH: 93
<212> TYPE: DNA
<213> ORGANISM: artificial sequence
<220> FEATURE:
<223> OTHER INFORMATION: synthetic construct -continued

<400> SEQUENCE: 46

```
cgttacgagc ttgagtacaa gcttcatatg tatatctcct tcttaaagtt aaacaaaatt     60

atttctagtg ggaaaaccgt tgtggtctcc cac                                  93
```